United States Patent
Haacke et al.

(10) Patent No.: US 11,249,159 B2
(45) Date of Patent: Feb. 15, 2022

(54) SYSTEMS AND METHODS FOR ENHANCEMENT OF RESOLUTION FOR STRATEGICALLY ACQUIRED GRADIENT ECHO (STAGE) IMAGING

(71) Applicant: SPINTECH, INC., Bingham Farms, MI (US)

(72) Inventors: E. Mark Haacke, Detroit, MI (US); Yongsheng Chen, Detroit, MI (US)

(73) Assignee: SPINTECH, INC., Bingham Farms, MI (US)

( * ) Notice: Subject to any disclaimer, the term of this patent is extended or adjusted under 35 U.S.C. 154(b) by 0 days.

(21) Appl. No.: 16/899,357

(22) Filed: Jun. 11, 2020

(65) Prior Publication Data
US 2021/0389401 A1    Dec. 16, 2021

(51) Int. Cl.
  *G01V 3/00*    (2006.01)
  *G01R 33/48*   (2006.01)
  *A61B 5/055*   (2006.01)
  *G01R 33/56*   (2006.01)
  *G01R 33/561*  (2006.01)

(52) U.S. Cl.
  CPC .......... *G01R 33/4826* (2013.01); *A61B 5/055* (2013.01); *G01R 33/5608* (2013.01); *G01R 33/5615* (2013.01)

(58) Field of Classification Search
  CPC .............. G01R 33/543; G01R 33/5659; G01R 33/3415; G01R 33/36; A61B 5/055
  USPC ......................................................... 324/309
  See application file for complete search history.

(56) References Cited

U.S. PATENT DOCUMENTS

| | | | |
|---|---|---|---|
| 6,804,546 B1* | 10/2004 | Thompson | G01R 33/56 324/306 |
| 10,451,697 B2 | 10/2019 | Haacke | |
| 2011/0034176 A1* | 2/2011 | Lord | G06K 9/6253 455/450 |
| 2014/0070804 A1* | 3/2014 | Huang | G01R 33/56 324/309 |
| 2016/0252597 A1* | 9/2016 | Liu | A43B 3/00 324/309 |

(Continued)

OTHER PUBLICATIONS

Chen Y, Liu S, Wang Y, Kang Y, Haacke EM. STrategically Acquired Gradient Echo (STAGE) imaging, part I: Creating enhanced T1 contrast and standardized susceptibility weighted imaging and quantitative susceptibility mapping. Magn. Reson. Imaging 2018;46:130-139. doi: 10.1016/j.mri.2017.10.005.

(Continued)

*Primary Examiner* — Walter L Lindsay, Jr.
*Assistant Examiner* — Frederick Wenderoth
(74) *Attorney, Agent, or Firm* — Foley & Lardner LLP

(57) ABSTRACT

Systems and methods for high-resolution STAGE imaging can include acquisition of relatively low-resolution k-space datasets with two separate multi-echo GRE sequences. The multi-echo GRE sequences can correspond to separate and distinct flip angles. Various techniques for combining the low-resolution k-space datasets to generate a relatively high-resolution k-space are described. These techniques can involve combining low-resolution k-space datasets associated with various echo types. The STAGE imaging approaches described herein allow for rapid imaging, enhanced image resolution with relatively small or no increase in MR data acquisition time.

22 Claims, 11 Drawing Sheets

(56) References Cited

U.S. PATENT DOCUMENTS

2019/0369193 A1* 12/2019 Kobayashi ....... G01R 33/56563

OTHER PUBLICATIONS

Do, Won-Joon, Seung Hong Choi, and Sung-Hong Park. "Simultaneous Variable-Slab Dual-Echo TOF MR Angiography and Susceptibility-Weighted Imaging." IEEE transactions on medical imaging 37.7 (2018): 1632-1640.

Wang Y, Chen Y, Wu D, Wang Y, Sethi SK, Yang G, Xie H, Xia S, Haacke EM. STrategically Acquired Gradient Echo (STAGE) imaging, part II: Correcting for RF inhomogeneities in estimating T1 and proton density. Magn Reson Imaging 2018;46:140-50. doi: 10.1016/j.mri.2017.10.006.

* cited by examiner

SYSTEMS AND METHODS FOR ENHANCEMENT OF RESOLUTION FOR STRATEGICALLY ACQUIRED GRADIENT ECHO (STAGE) IMAGING

BACKGROUND OF THE DISCLOSURE

The present disclosure relates generally to the field of magnetic resonance imaging (MRI). Specifically, this disclosure relates to methods and systems for improving the resolution of strategically acquired gradient echo (STAGE) imaging that involves the use of more than one flip angle.

Magnetic resonance imaging (MRI) is an imaging modality that uses magnetic fields to reconstruct an image representing part or all of the scanned object or person of interest. An MRI scanner includes a magnet for generating a strong static magnetic field, such as a magnetic field in the range of 0.05 Tesla (T) to 20 T, and radio frequency (RF) transceivers for transmitting and/or receiving RF signals. When a body is placed in the generated static magnetic field, the hydrogen protons within the body align to the magnetic field. An RF pulse is applied in the form of an oscillating B1 field to tip the spins so that there is a bulk magnetization remaining in the transverse field. When the RF pulse is turned off, the hydrogen protons gradually realign with the static magnetic field. The RF receiver coils detect the precessing magnetization and from it create a measurable current. At predefined time points, referred to as the sampling time, echo time (TE), or gradient echo time, data are collected and sampled and used to reconstruct an image of the scanned body or a part thereof.

SUMMARY OF THE DISCLOSURE

According to at least one aspect, a magnetic resonance imaging (MRI) system can include an MRI scanner, at least one processor, and a memory, with computer code instructions stored thereon. The MRI scanner can acquire, for a first flip angle, a first magnetic resonance (MR) k-space dataset and a second MR k-space dataset by scanning an anatomical region of interest with at least two echo times. The MRI scanner can acquire the first MR k-space dataset at a first TE1 echo time and acquire the second MR k-space dataset at a first TE2 echo time. The MRI scanner can acquire, for a second flip angle, a third MR k-space dataset and a fourth MR k-space dataset by scanning the anatomical region of interest with the at least two echo times. The MRI scanner can acquire the third MR k-space dataset at a second TE1 echo time and acquire the fourth MR k-space dataset at a second TE2 echo time. The computer code instructions, when executed by the at least one processor, can cause the at least one processor to generate a fifth MR k-space dataset by combining the fourth MR k-space dataset with either (i) the second MR k-space dataset or (ii) a central extrapolation of the third MR k-space dataset. The at least one processor can reconstruct an MR image of the anatomical region of interest using the fifth MR k-space dataset.

The at least one processor can be configured to reconstruct a susceptibility-weighted image using the MR image of the anatomical region. The at least one processor can be configured to reconstruct a quantitative susceptibility mapping (QSM) image using the MR image of the anatomical region. In reconstructing the MR image of the anatomical region of interest, the at least one processor can be configured to compute an inverse Fourier transform of the fifth MR k-space dataset. In some implementations, the first flip angle can be equal to 6 degrees and the second flip angle can be equal to 24 degrees.

The at least one processor can, in combining the second MR k-space dataset and the fourth MR k-space dataset, use the second MR k-space dataset to generate a central portion of the fifth MR k-space dataset and use the fourth MR k-space dataset to generate two opposite outer portions of the fifth MR k-space dataset. The central portion of the fifth MR k-space dataset can (i) partially overlap with a first outer portion of the two opposite outer portions of the fifth MR k-space dataset along a first overlap region, and (ii) partially overlap with a second outer portion of the two opposite outer portions of the fifth MR k-space dataset along a second overlap region.

The at least one processor can generate a second MR image by using an inverse Fourier transform of the first MR k-space dataset, and generate a third MR image by using an inverse Fourier transform of the second MR k-space data set. The at least one processor can complex divide the third MR image by the second MR image to obtain a phase difference image and a T2* weighting factor. The at least one processor can generate a fourth MR image by using an inverse Fourier transform of the third MR k-space data set. The at least one processor can adjust, using the phase difference image and the T2* weighting factor, the fourth MR image to generate a fifth MR image. The at least one processor can Fourier transform the fifth MR image to obtain the central k-space extrapolation of the third MR k-space dataset. The at least one processor can generate the fifth MR k-space dataset by combining the central extrapolation of the third MR k-space dataset and the fourth MR data k-space dataset. The central extrapolation of the third MR k-space dataset can be used to generate a central portion of the fifth MR k-space dataset and the fourth MR k-space dataset can be used to generate two opposite outer portions of the fifth MR k-space dataset. The at least one processor can apply inverse Fourier transform to the fifth MR k-space dataset to reconstruct the MR image of the anatomical region of interest. The central extrapolation of the third MR k-space dataset can (i) partially overlap with a first outer portion of the two opposite outer portions of the fifth MR k-space dataset along a first overlap region, and (ii) partially overlap with a second outer portion of the two opposite outer portions of the fifth MR k-space dataset along a second overlap region.

In combining the second MR k-space dataset and the fourth MR k-space dataset, the at least one processor can use the second MR k-space dataset to generate a first side portion of the fifth MR k-space dataset and use the fourth MR k-space dataset to generate a second side portion of the fifth MR k-space dataset. The first side portion can be to opposite to the second side portion. The first side portion of the fifth MR k-space dataset can partially overlap with the second side portion of the fifth MR k-space dataset along an overlap region.

In generating the fifth MR k-space dataset, the at least one processor can be configured to generate a second MR image by using an inverse Fourier transform of the second MR k-space data set and generate a third MR image by using an inverse Fourier transform of the third MR k-space data set. The at least one processor can compare phase information of the second MR image to phase information of the third MR image. The at least one processor can adjust, based on the comparison, the phase information of the third MR image so that the adjusted phase information of the third MR image is equal to the phase information of the second MR image. The at least one processor can generate a sixth MR k-space dataset by applying a Fourier transform to the third MR image with the adjusted phase information. The at least one processor can generate the fifth MR k-space dataset by combining the second MR k-space dataset and the sixth MR k-space dataset within the overlap region.

According to at least one aspect, a method for magnetic resonance imaging (MRI) can include an MRI scanner acquiring, for a first flip angle, a first magnetic resonance (MR) k-space dataset and a second MR k-space dataset by scanning an anatomical region of interest with at least two echo times. The MRI scanner can acquire the first MR k-space dataset at a first TE1 echo time and the second MR k-space dataset at a first TE2 echo time. The method can include the MRI scanner acquiring, for a second flip angle, a third MR k-space dataset and a fourth MR k-space dataset by scanning the anatomical region of interest with the at least two echo times. The MRI scanner can acquire the third MR k-space dataset at a second TE1 echo time and acquire the fourth MR k-space dataset at a second TE2 echo time. The method can include the MRI scanner generating a fifth MR k-space dataset by combining the fourth MR k-space dataset with either (i) the second MR k-space dataset or (ii) a central extrapolation of the third MR k-space dataset. The method can include the MRI scanner reconstructing an MR image of the anatomical region of interest using the fifth MR k-space dataset.

The method can include reconstructing a susceptibility-weighted image using the MR image of the anatomical region. The method can also include reconstructing a quantitative susceptibility mapping (QSM) image using the MR image of the anatomical region. Reconstructing the MR image of the anatomical region of interest can include computing an inverse Fourier transform of the fifth MR k-space dataset. The first flip angle can be equal to 6 degrees and the second flip angle can be equal to 24 degrees.

Combining the second MR k-space dataset and the fourth MR k-space dataset can include using the second MR k-space dataset to generate a central portion of the fifth MR k-space dataset, and using the fourth MR k-space dataset to generate two opposite outer portions of fifth MR k-space dataset. The central portion of the fifth MR k-space dataset (i) can partially overlap with a first outer portion of the two opposite outer portions of the fifth MR k-space dataset along a first overlap region, and (ii) can partially overlap with a second outer portion of the two opposite outer portions of the fifth MR k-space dataset along a second overlap region.

The method can include generating a second MR image by using an inverse Fourier transform of the first MR k-space dataset, and generating a third MR image by using an inverse Fourier transform of the second MR k-space data set. The method can include complex dividing the third MR image by the second MR image to obtain a phase difference image and a T2* weighting factor. The method can include generating a fourth MR image by using an inverse Fourier transform of the third MR k-space data set. The method can include adjusting, using the phase difference image and the T2* weighting factor, the fourth MR image to generate a fifth MR image. The method can include Fourier transforming the fifth MR image to obtain the central k-space extrapolation of the third MR k-space dataset. The method can include generating the fifth MR k-space dataset by combining the central extrapolation of the third MR k-space dataset and the fourth MR data k-space dataset. The central extrapolation of the third MR k-space dataset can be used to generate a central portion of the fifth MR k-space dataset and the fourth MR k-space dataset can be used to generate two opposite outer portions of the fifth MR k-space dataset. The method can include applying inverse Fourier transform to the fifth MR k-space dataset to reconstruct the MR image of the anatomical region of interest. The central extrapolation of the third MR k-space dataset can (i) partially overlap with a first outer portion of the two opposite outer portions of the fifth MR k-space dataset along a first overlap region, and (ii) partially overlap with a second outer portion of the two opposite outer portions of the fifth MR k-space dataset along a second overlap region.

Combining the second MR k-space dataset and the fourth MR k-space dataset can include using the second MR k-space dataset to generate a first side portion of the fifth MR k-space dataset, and using the fourth MR k-space dataset to generate a second side portion of the fifth MR k-space dataset. The first side portion can be opposite to the second side portion. The first side portion of the fifth MR k-space dataset can partially overlap with the second side portion of the fifth MR k-space dataset along an overlap region.

Generating the fifth MR k-space dataset can include generating a second MR image by using an inverse Fourier transform of the second MR k-space dataset and generating a third MR image by using an inverse Fourier transform of the fourth MR k-space data set. The method can include comparing phase information of the second MR image to phase information of the third MR image. The method can include adjusting, based on the comparison, the phase information of the third MR image so that the adjusted phase information of the third MR image is equal to the phase information of the second MR image. The method can include generating a sixth MR k-space dataset by applying a Fourier transform to the third MR image with the adjusted phase information. The method can include generating the fifth MR k-space dataset by combining the second MR k-space dataset and the sixth MR k-space dataset within the overlap regions.

According to at least one aspect, a computer-readable medium can include computer code instructions stored thereon. The computer code instructions, when executed by at least one processor, can cause the at least one processor to cause a magnetic resonance imaging (MRI scanner to acquire, for a first flip angle, a first magnetic resonance (MR k-space dataset and a second MR k-space dataset by scanning an anatomical region of interest with at least two echo times. The first MR k-space dataset can be acquired at a first TE1 echo time and the second MR k-space dataset can be acquired at a first TE2 echo time. The at least one processor can cause the MRI scanner to acquire, for a second flip angle, a third MR k-space dataset and a fourth MR k-space dataset by scanning the anatomical region of interest with the at least two echoes times. The third MR k-space dataset can be acquired at a second TE1 echo time and the fourth MR k-space dataset can be acquired at a second TE2 echo time. The at least one processor can generate a fifth MR k-space dataset by combining the fourth MR k-space dataset with either (i) the second MR k-space dataset or (ii) a central extrapolation of the third MR k-space dataset. The at least one processor can reconstruct an MR image of the anatomical region of interest using the fifth MR k-space dataset.

According to at least one aspect, a magnetic resonance imaging (MRI) system can include an MRI scanner, at least one processor, and a memory, with computer code instructions stored thereon. The MRI scanner can acquire, for a first flip angle, a first magnetic resonance (MR) k-space dataset of an anatomical region of interest. The MRI scanner can acquire, for a second flip angle, a second MR k-space dataset of the anatomical region of interest. The computer code instructions, when executed by the at least one processor, can cause the at least one processor to generate a third MR k-space dataset by combining the first MR k-space dataset and the second MR k-space dataset. The at least one processor can reconstruct an MR image of the anatomical region of interest using the third MR k-space dataset.

According to at least one aspect, a method for magnetic resonance imaging (MRI) can include an MRI scanner acquiring, for a first flip angle, a first magnetic resonance (MR) k-space dataset of an anatomical region of interest. The method can include the MRI scanner acquiring, for a second flip angle, a second MR k-space dataset of the anatomical region of interest. The method can include the MRI scanner generating a third MR k-space dataset by combining the first MR k-space dataset and the second MR k-space dataset. The method can include the MRI scanner reconstructing an MR image of the anatomical region of interest using the third MR k-space dataset.

According to at least one aspect, a computer-readable medium can include computer code instructions stored thereon. The computer code instructions, when executed by at least one processor, can cause the at least one processor to cause an MRI scanner to acquire, for a first flip angle, a first magnetic resonance (MR) k-space dataset of an anatomical region of interest. The at least one processor can cause the MRI scanner to acquire, for a second flip angle, a second MR k-space dataset of the anatomical region of interest. The computer code instructions, when executed by the at least one processor, can cause the at least one processor to generate a third MR k-space dataset by combining the first MR k-space dataset and the second MR k-space dataset. The at least one processor can reconstruct an MR image of the anatomical region of interest using the third MR k-space dataset.

DETAILED DESCRIPTION

Figure 1:
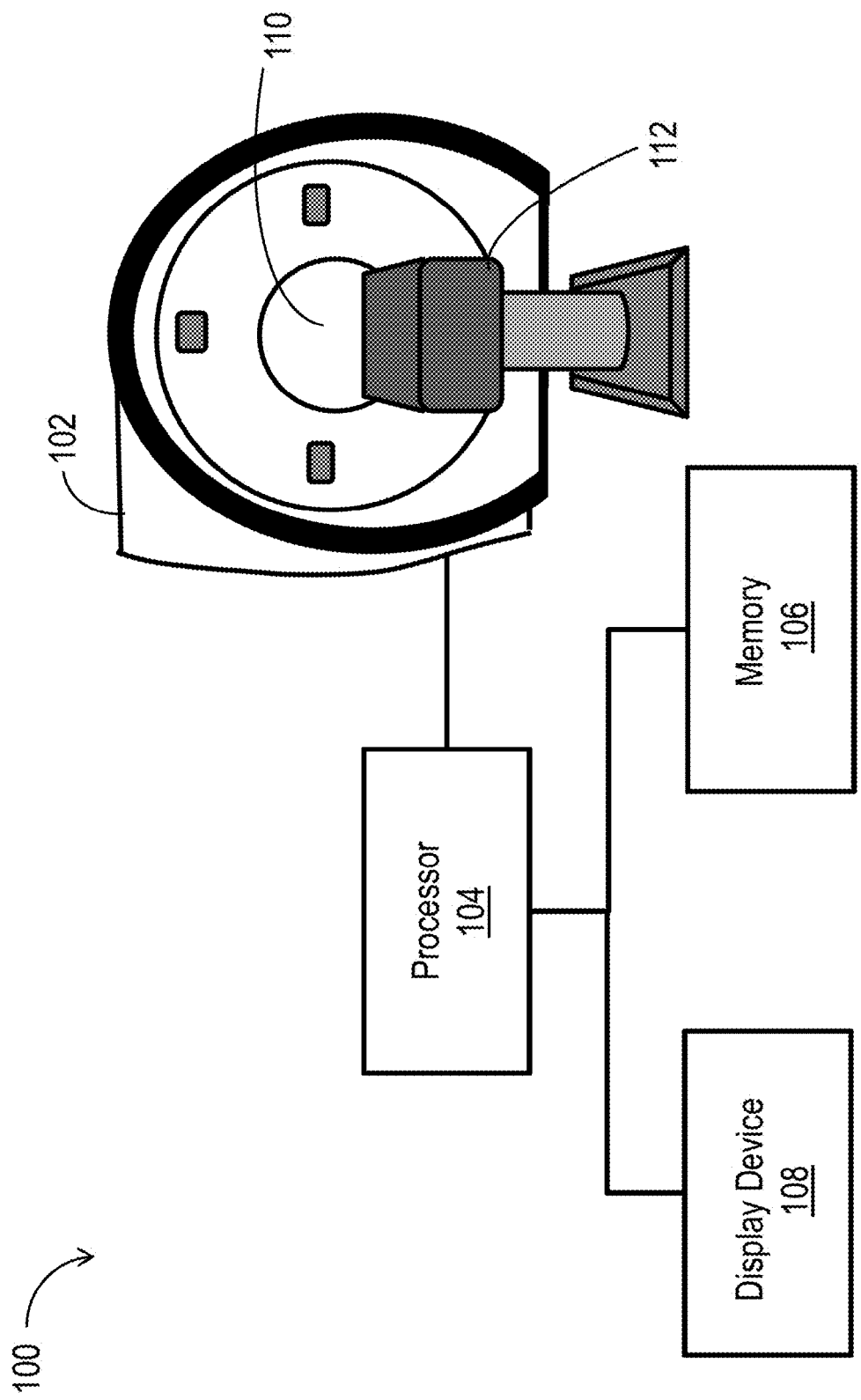
FIG. 1 is a block diagram illustrating a magnetic resonance imaging (MRI) system, according to inventive concepts of this disclosure.

Strategically acquired gradient echo (STAGE) imaging is a rapid multi-contrast imaging method used to collect clinical data very quickly usually in less than 5 minutes, for a typical implementation at 3 T, depending on the desired resolution. In some implementations, data acquisition can take more than 5 minutes if a relatively high resolution is sought. A magnetic resonance (MR) imaging system can use two different flip angles to create, for example, proton spin density weighted (PDW) images and T1W images. The MR data can be collected with a short repetition time (TR) on the order of 25 ms and with flip angles of 6° (e.g., for PDW images) and 24° (e.g., for T1W images) at 3 T. It should be noted that other TR and/or other flip angles can be used. Collecting MR data at separate sequences corresponding to distinct flip angles can lead to MR data with different contrast. The difference in contrast usually means that information from the two sequences (or scans) would result in poor image quality or undesired image artifacts if combined or merged together. However, here, various embodiments of STAGE imaging that involve combining k-space datasets corresponding to distinct flip angles are described and illustrated for both phase data and for some combinations of magnitude data as well.

An example application, the concept of data sharing (or merging) across dual echo (or multi-echo) sequences corresponding to distinct flip angles can be used to create susceptibility weighted imaging (SWI) data. SWI has played a role in more than 1000 studies since its inception. The use of SWI relies to a large degree on collecting the data with the right resolution, usually a higher resolution than that collected in the existing rapid STAGE protocol. Such low resolution does not reveal the small veins well and, hence, does not satisfy the needs of most clinical studies with SWI or for quantitative susceptibility mapping (QSM). The STAGE imaging approaches described herein alleviates this problem by doubling (or increasing) the in-plane resolution of the second echo (or later echoes) data to achieve higher quality SWI and QSM images. While one would expect the resulting increase in resolution would lead to a proportional increase in data acquisition time, the STAGE imaging approaches described herein have little or no impact on the time duration of the MR data acquisition. Both SWI and QSM are important for studying calcifications, asymmetrically prominent cortical veins (for stroke), damaged veins in traumatic brain injury (TBI), iron measurements (for multiple sclerosis and Parkinson's disease) and oxygen saturation measurements (for stroke).

In the current disclosure, several k-space sharing (or merging) techniques provide relatively high resolution SWI and QSM while maintaining rapid scan time. These techniques can include acquiring the high frequency and low frequency k-space datasets in, respectively, a first dual-echo (or multi-echo) gradient echo (GRE) sequence corresponding to a first flip angle (e.g., 6 degrees) and a second dual-echo (or multi-echo) GRE sequence corresponding to a second flip angle (e.g., 24 degrees). The STAGE imaging approaches described herein can be referred to as high resolution SWI STAGE (HR-SWI-STAGE). The STAGE imaging approaches described herein also address the case where MR data acquired at distinct dual-echo (or multi-echo) GRE sequences are associated with different contrast.

The STAGE imaging techniques described herein involve data acquisition for two dual-echo (or multi-echo) GRE sequences corresponding to two different flip angles. The total acquisition time can be around 5 minutes, for example, with the parameters listed in Table 1 below. To assess the performance of the STAGE imaging approaches described herein, a fully sampled high-resolution data set was collected. Subsets of the collected data are used as low-resolution k-space datasets. The low-resolution k-space datasets represent only portions of the corresponding k-spaces. Combining the different k-space coverages as described herein allows for creating a high resolution k-space coverage that can then be inverse Fourier transformed to create a high-resolution MR image. The STAGE imaging techniques described herein result in little to no increase in data acquisition time.

In the current disclosure, methods and systems for STAGE imaging with improved image resolution are described. The STAGE imaging techniques described herein allow for rapid imaging, enhanced image resolution and/or improved SNR by using acquired k-space datasets corresponding to distinct flip angles.

TABLE 1

Example STAGE imaging parameters for 3T.

|  | Axial Dual-echo GRE | Axial Dual-echo GRE |
| --- | --- | --- |
| Read × Phase FOV (mm) | 256 × 192 | 256 × 192 |
| Scanning matrix | 384 × 144 | 384 × 144 |
| Voxel size (mm$^3$) | 0.67 × 1.33 × 2.0 | 0.67 × 1.33 × 2.0 |
| Number of slices | 64 | 64 |
| Slice oversampling | 12.5% | 12.5% |
| TR (ms) | 25 | 25 |
| IEs (ms) | 7.5, 17.5 | 7.5, 17.5 |
| FA (degree) | 6 | 24 |
| Sampling bandwidth (Hz/pixel) | 240 | 240 |
| Fully flow compensation | Yes | Yes |
| Acc. Factor (GRAPPA) | 2 | 2 |
| TA (min:sec) | 2:29 | 2:29 |

FIG. 1 is a block diagram illustrating an MRI system 100, according to inventive concepts of this disclosure. In brief overview, the MRI system 100 can include an MRI scanner 102, a processor 104, a memory 106, and a display device 108. The processor 104 can be communicatively coupled to the MRI scanner 102, the memory 106 and the display device 108. In some implementations, the processor 104, the memory 106, the display device 108 or a combination thereof can be components of the MRI scanner 102. The MRI scanner 102 can include a magnet (not shown in FIG. 1) for generating a relatively strong static magnetic field, such as a magnetic field in the range of 0.05 Tesla (T) to 20 T. The magnet can have a cylindrical shape forming a cavity 110 designed to receive a patient or other subject. The MRI scanner 102 can include a sliding table 110. The patient can lie down on the sliding table 112, and the position of the sliding table 112 can be adjusted such that an anatomical region of interest of the patient, e.g., the patient's head or chest, falls within the cavity 110 and is subjected to the magnetic field generated by the magnet.

The MRI scanner 102 can include a plurality of radio frequency (RF) coils (not shown in FIG. 1) for transmitting and/or receiving RF signals. The RF coils can include transmit RF coils and receive RF coils. The RF transmit coils can emit RF pulses to excite the anatomical region of interest of the patient, according to an MRI pulse sequence. The receive RF coils can record MRI signals generated by the anatomical region of interest following completion of the RF transmit pulse. The RF coils may include RF transceivers capable of alternately transmitting and receiving RF signals. The RF coils can include gradient coils designed to induce gradients, or distortions, in the main magnetic field generated by the magnet in a predictable or a predefined way to make spatial separation of the different spatial components of the object uniquely. Specifically, the gradient coils can include frequency-encoding gradients and phase-encoding gradients.

The imaging system 100 can include one or more processors 104. The one or more processors 104 can include a processor integrated within the MRI scanner 102, a processor of a computing device communicatively coupled to the MRI scanner 102, or a combination thereof. The memory 106 can include a memory component of the MRI scanner 102, a memory component of a computing device communicatively coupled to the MRI scanner 102, or a combination thereof. The memory 106 can include computer executable instructions, which when executed by the one or more processors 104, can cause the one or more processors 104 to perform methods for STAGE imaging described herein. The memory 106 can store MRI data acquired by the MRI scanner 102, and the processor(s) 104 can access such data from the memory 106. The memory 106 can receive and store images generated by the processor(s) 104 based on the MRI data acquired by the scanner 102.

The display device 108 can include a cathode ray tube (CRT) display, a light emitting diode (LED) display, an organic light emitting diode (OLED) display, a plasma display panel (PDP), a liquid crystal display (LCD), or other display known to a person of ordinary skill in the art. The display device 108 may be a stand-alone device or a display of a computing device (e.g., a desktop, laptop, or tablet) communicatively coupled to the MRI scanner 102. The display device 108 can include a touch screen. The display device 108 can receive image data from the processor 104 or the memory 106 and display the received image data. For example, upon reconstructing MRI images based on data acquired by the MRI scanner 102, the processor 104 can provide the reconstructed images for display on the display device 108.

Figure 2:
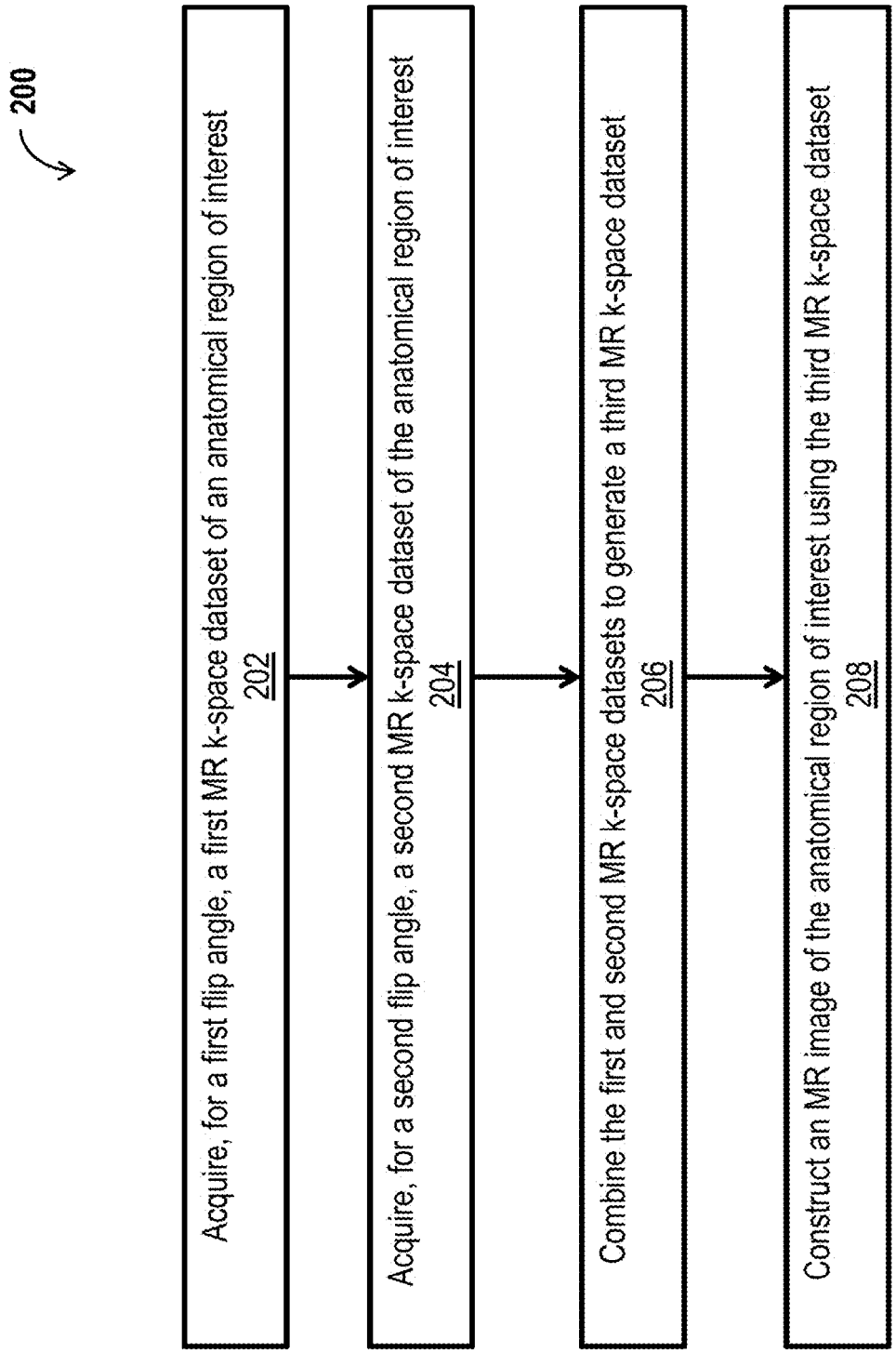
FIG. 2 is a flowchart illustrating a method of strategically acquired gradient echo (STAGE) imaging, according to inventive concepts of this disclosure.

FIG. 2 is a flowchart illustrating a method 200 of strategically acquired gradient echo (STAGE), according to inventive concepts of this disclosure. In brief overview, the method 200 can include acquiring a first MR k-space dataset of an anatomical region of interest corresponding to a first flip angle (STEP 202), and acquiring a second MR k-space dataset of the anatomical region of interest corresponding to a second flip angle (STEP 204). The method 200 can include generating a third MR k-space dataset by combining the first MR k-space dataset and the second MR k-space dataset (STEP 206). The method 200 can include constructing an MR image of the anatomical region of interest using the third MR k-space dataset (STEP 208).

The method 200 can include the MRI scanner 102 acquiring the first MR k-space dataset corresponding to the first flip angle (STEP 202), and acquiring the second MR k-space dataset of the anatomical region of interest corresponding to a second flip angle (STEP 204). The RF coils can emit RF pulses associated with first flip angle and RF pulses associated with the second flip angle. The repetition time TR can be in the order of 25 milliseconds (ms) or less. The emitted RF pulses for each flip angle can results in corresponding dual-echo (or multi-echo) GRE sequence. In a dual-echo GRE sequence, the two echo times can be defined as TE1 and TE2. In general, in a multi-echo GRE sequence, the echo times can be defined as TE1, TE2, TE3, . . . etc. Given the application of the frequency and phase encoding gradients, the MRI scanner 102 or the processor 104 can use the MR signals recorded at each echo time to fill or generate a corresponding k-space (or a corresponding k-space dataset).

The RF coils can be used to excite an arbitrary flip angle. The MRI scanner 102 can generate two GRE sequences with otherwise identical structure differing only by the flip angle applied at the beginning of the sequence. One implementation of the dual echo STAGE acquisition would be to collect the first k-space dataset for a first flip angle of 6 degrees and the second k-space dataset for a second flip angle of 24 degrees. In some implementations, the MRI scanner 102 can use other values for the first and second flip angles. The gradients can be used to generate two or more echoes. The MRI scanner 102 or the processor 104 can apply the inverse Fourier transform to the MR signals (effectively the k-space for a given echo) generate a corresponding MR image.

The method 200 can include the processor 104 generating a third MR k-space dataset by combining the first and second MR k-space datasets (STEP 206). The processor 104 can combine a first portion of the first MR k-space dataset and a second portion of the second MR k-space dataset to generate the third MR k-space dataset. The first and second portions can be disjoint or can partially overlap as is described in further detail below. In some implementations, the processor 104 can combine modified versions of the first and/or second MR k-space datasets to generate the third MR k-space dataset.

The method 200 can include the processor 104 constructing an MR image of the anatomical region of interest using the third MR k-space dataset (STEP 208). The processor 104 can construct the MR image by applying the inverse Fourier transform to the third MR k-space dataset. The third MR k-space dataset represents a fully sampled k-space, and as such, the reconstructed image has a higher resolution than an MR image reconstructed either using the usual central k-space acquired at an echo time (e.g., TE1 or TE2) of the first flip angle or using the usual central k-space acquired at a given echo time (e.g., TE1 or TE2) of the second flip angle. Specifically, the method 200 allows for a higher resolution MR image in half (or a fraction) of the usual acquisition time of the multi-flip-angle STAGE data.

The method 200 can be implemented in various ways, for example, depending on the number and portions of MR k-spaces acquired, the echo times at which the MR k-spaces are acquired, preprocessing (if any) applied to the acquired MR k-space datasets, the way portions of the MR k-spaces are combined, or a combination thereof. Two main approaches, namely approach I and approach II, for implementing the method 200 are discussed in further detail with regard to FIGS. 3-8. Each of these approaches, can be implemented according to various embodiments. Also, the MRI scanner 102 or the processor 104 can provide a user interface (UI), e.g., on the display device 108, to allow a user to select settings for MR data acquisition and the approach to be used to provide enhanced-resolution STAGE imaging based on multi-flip-angle MR data. The processor 102 can cause the MR scanner 102 to acquire MR data according to the selected settings. For example, the selected settings can indicate the values of the flip angles to be used, the number and/or values of echo times at which to record MR signals, the type of output images to be constructed, or a combination thereof. The processor 102 can construct output MR images according to the selected STAGE imaging approach(es), for example, among the methods described below with regard to FIGS. 3-8.

Approach I

Figure 3:
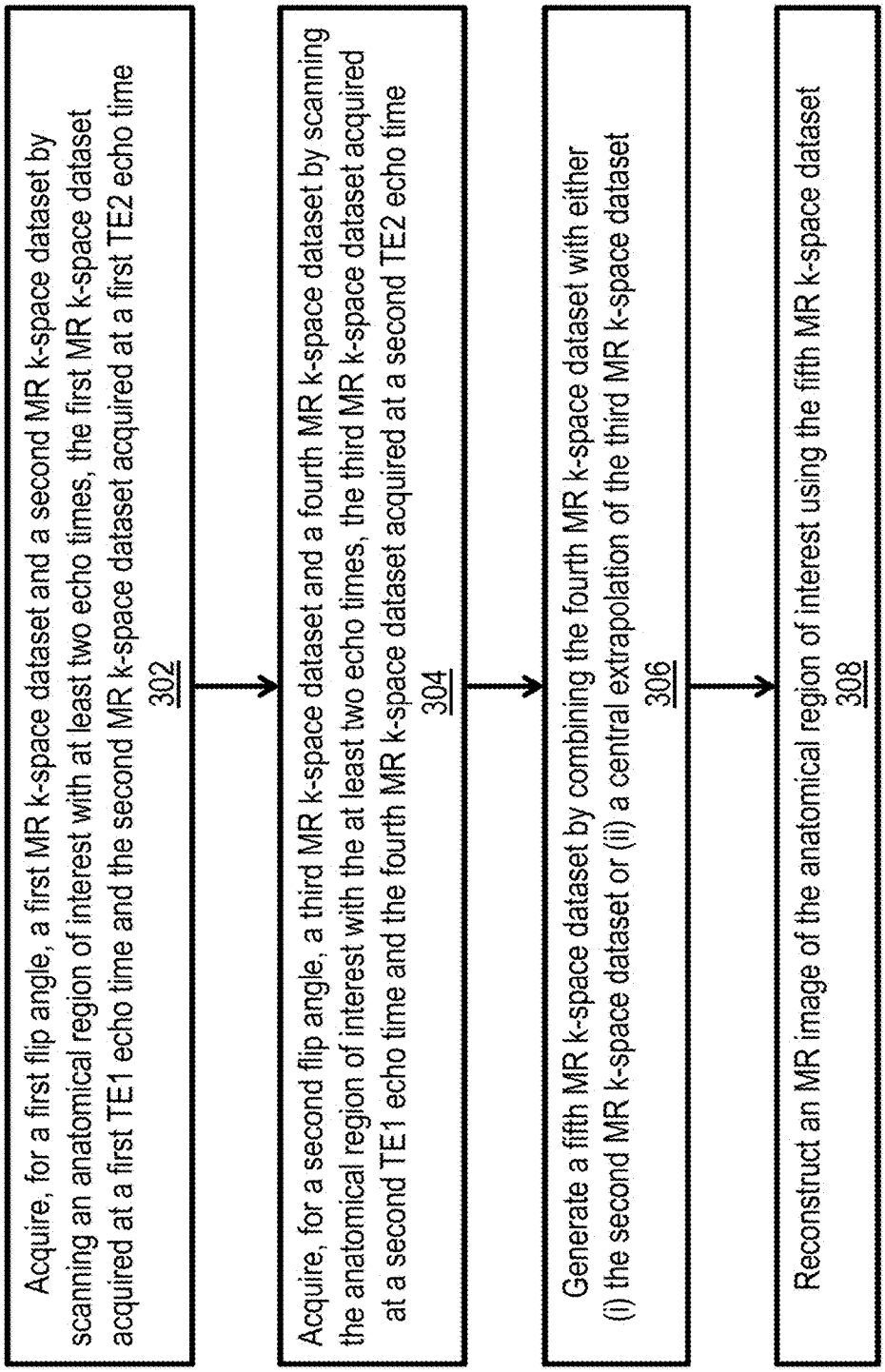
FIG. 3 is a flowchart illustrating another method of strategically acquired gradient echo (STAGE) imaging, according to inventive concepts of this disclosure.

Referring to FIG. 3, a flowchart illustrating another method 300 of STAGE imaging is shown, according to inventive concepts of this disclosure. In a brief overview, the method 300 can include acquiring, for a first flip angle, a first MR k-space dataset and a second MR k-space dataset by scanning an anatomical region of interest with at least two echo times TE1 and TE2 (STEP 302). The method 300 can include acquiring, for a second flip angle, a third MR k-space dataset and a fourth MR k-space dataset by scanning the anatomical region of interest with the at least two echo times TE1 and TE2 (STEP 304). The method 300 can include generating a fifth MR k-space dataset by combining the second and fourth MR k-space datasets (STEP 306). The method 300 can include constructing an MR image of the anatomical region of interest using the fifth MR k-space dataset (STEP 308).

Referring to FIGS. 1 and 3, the method 300 can include the MRI scanner 102 acquiring, for the first flip angle, the first MR k-space dataset and the second MR k-space dataset by scanning an anatomical region of interest with at least two echo times TE1 and TE2 (STEP 302), and acquiring, for a second flip angle, a third MR k-space dataset and a fourth MR k-space dataset by scanning the anatomical region of interest with the at least two echo times TE1 and TE2 (STEP 304). The MRI scanner 102 can acquire the first MR k-space dataset at the TE1 echo time associated with the first flip angle, and acquire the second MR k-space dataset at the TE2 echo time associated with the first flip angle. For instance, the MRI scanner 102 or the corresponding RF coils can excite a dual-echo (or a multi-echo) GRE sequence by, for example, alternating between emitting a first MR pulse associated with the first flip angle and a second MR pulse associated with the second flip angle. The RF coils can receive a signal, for example, at each repetition time TR, for first and second sets at the TE1 and TE2 echo times associated with the first flip angle, respectively. The RF coils can also receive a signal for third and fourth sets at the TE1 and TE2 echo times associated with the second flip angle, respectively. The MRI scanner 102 or the processor 104 can generate a first TE1 k-space dataset using the first set of MR signals recorded at the TE1 echo time of the first flip angle, and a first TE2 k-space dataset using the second set of MR signals recorded at the TE2 echo time of the first flip angle. The MRI scanner 102 or the processor 104 can generate also a second TE1 k-space dataset using the third set of MR signals recorded at the TE1 echo time of the second flip angle, and a second TE2 k-space dataset using the fourth set of MR signals recorded at the TE2 echo time of the second flip angle.

Figure 4A:
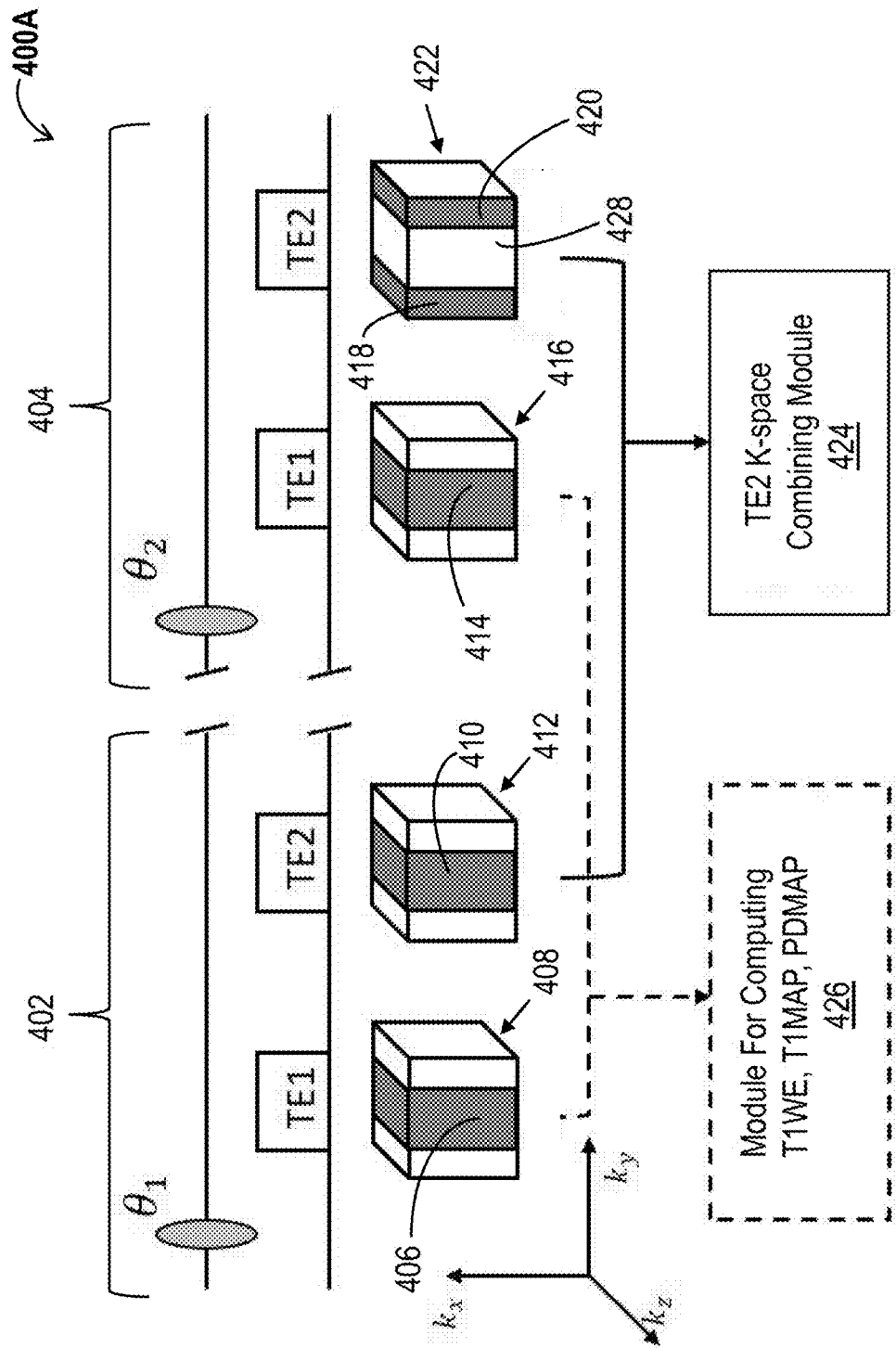
FIGS. 4A and 4B show block diagrams depicting example approaches for acquiring and combining MR data corresponding to multiple flip angles, according to inventive concepts of this disclosure.

Referring to FIG. 4A, a block diagram 400A depicting an example embodiment for acquiring and combining MR data corresponding to multiple flip angles, according to inventive concepts of this disclosure. The diagram 400A illustrates two blocks 402 and 404 of a dual-echo GRE sequence having two flip angles $\theta_1$ and $\theta_2$. The first block 402 corresponds to the first flip angle $\theta_1$, while the second block 404 corresponds to the second flip angle $\theta_2$. During the first block 402, the MRI scanner 102 can acquire the first TE1 k-space dataset representing a central portion 406 (shown in gray) of the corresponding TE1 k-space 408, and acquire a first TE2 k-space dataset representing a central portion 410 (shown in gray) of the corresponding TE2 k-space 412. During the second block 404, the MRI scanner 102 can acquire a second TE1 k-space dataset representing a central portion 414 (shown in gray) of the corresponding TE1 k-space 416, and acquire a second TE2 k-space dataset representing two opposite side portions 418 and 420 (shown in gray) of the corresponding TE2 k-space 422.

In summary, the MRI scanner 102 can acquire data for the k-space portions (or regions) 406, 410, 414, 418 and 420 shown in gray in FIG. 4A. Acquiring these portions of the k-spaces 408, 412, 416 and 422 can make the MR data acquisition relatively faster, for example, compared to full acquisition of the corresponding k-space. The TE1 k-space portions 406 and 414 can have the same k-space coverage. The TE2 k-space portion 410 can correspond to a k-space coverage adjacent to but disjoint from (i.e., does not overlap with) the k-space coverage of the TE2 k-space portions 418 and 420. For instance, combining the TE2 k-space portion 410 with the TE2 k-space portions 418 and 420 can result in full k-space coverage with higher resolution than the central k-space collected for the first echoes. For example, let the voxels of the full k-spaces 408, 412, 416 and 422 run between $-L\Delta k_y$ and $(L-1)\Delta k_y$ along the $k_y$ axis, where $\Delta k_y$ represents the step size in k-spaces along the $k_y$ axis. As such, the total number of steps to acquire a full k-space representing the center of k-space is equal to 2L. However, acquiring the k-space portions 406, 410 and 414 representing the central regions of k-spaces 408, 416 and 416, respectively, can be achieved in $2n$ steps where the central regions 406, 410 and 414 are defined by sampled k-space points with $k_y$-coordinate k satisfying $-n\Delta k_y \leq k \leq (n-1)\Delta k_y$. In this case, the integer n can be equal to the integer L/2. The k-space portion 418 of the TE2 k-space 422 can be defined by the sampled k-space points falling between $-L\Delta k_y$ and $-(n+1)\Delta k_y$ along the $k_y$ axis. The k-space portion 420 of the TE2 k-space 422 can be defined by the sampled k-space points falling between $n\Delta k_y$ and $(L-1)\Delta k_y$ along the $k_y$ axis.

Let $S_{\theta 1, TE2}$ be the k-space 412 corresponding to the first flip angle $\theta_1$ and the echo time TE2, and let $S_{\theta 2, TE2}$ be the k-space 422 corresponding to the second flip angle $\theta_2$ and the echo time TE2. In generating the TE2 k-space dataset corresponding to the k-space portion 410, the MRI scanner 102 can acquire data points $S_{\theta 1, TE2}(k)$ for $-n\Delta k_y \leq k \leq (n-1)\Delta k_y$ along the $k_y$ axis. Also, in generating the TE2 k-space dataset corresponding to the k-space portions 418 and 420, the MRI scanner 102 can acquire only data points $S_{\theta 2, TE2}(k)$ for $-L\Delta k_y \leq k \leq -(n+1)\Delta k_y$ and $n\Delta k_y \leq k \leq (L-1)\Delta k_y$.

Referring now to FIGS. 3 and 4A, the method 300 can include generating a fifth MR k-space dataset by combining the second and fourth MR k-space datasets (STEP 306). The processor 104 or the TE2 k-space combining module 424 can combine the TE2 k-space dataset acquired at STEP 302 for the first flip angle $\theta_1$ and the TE2 k-space dataset acquired at STEP 304 for the second flip angle $\theta_2$ to generate the fifth MR k-space dataset. The TE2 k-space combining module 424 can be a component of the MR imaging system 100 or the MRI scanner 102. The TE2 k-space combining module 424 can be a software component executable by the processor 104, a hardware component or circuit, or a combination of software and hardware components. Let $S_{\theta 1, \theta 2, TE2}$ be the final high resolution k-space corresponding to the fifth MR k-space dataset generated by combining the TE2 k-space dataset acquired at STEP 302 and corresponding to the first flip angle $\theta_1$ and the echo time TE2, and the TE2 k-space dataset acquired at STEP 304 and corresponding to the second flip angle $\theta_2$ and the echo time TE2. The processor 104 or the TE2 k-space combining module 424 can generate the final full resolution k-space dataset as:

$$S_{\theta_1,\theta_2,TE2}(k) = \begin{cases} S_{\theta_2,TE2}(k) & \text{if } -L\Delta k_y \leq k \leq -(n+1)\Delta k_y \\ S_{\theta_1,TE2}(k) & \text{if } -n\Delta k_y \leq k \leq (n-1)\Delta k_y \\ S_{\theta_2,TE2}(k) & \text{if } n\Delta k_y \leq k \leq (L-1)\Delta k_y \end{cases} \quad (1)$$

The fifth k-space dataset as defined in equation (1) represents a full k-space coverage for the high resolution reconstruction of $S_{\theta 1, \theta 2, TE2}$ that is formed by combining the TE2 k-space dataset corresponding to the k-space portion 410 and the TE2 k-space dataset corresponding to the k-space portions 418 and 420.

The fifth MR k-space dataset represents higher resolution MR data compared to the first and second MR k-space datasets (i.e., the TE2 k-space datasets acquired at STEPs 302 and 304) used to generate the MR k-space dataset because it now has a total of 2L k-space data points. Specifically, a MR image that represents the inverse Fourier transform of the fifth MR k-space dataset has a higher resolution than an MR image constructed using either of the TE2 k-space datasets acquired at STEP 302 or STEP 304. The MRI scanner 102 can employ the combining of TE2 k-space datasets corresponding to multiple flip angles to generate relatively high resolution (e.g., compared to the resolution of the acquired MR data) susceptibility weighted (SWI) images, high resolution true-SWI (tSWI) images, high resolution quantitative susceptibility mapping (QSM) images, or a combination thereof, among others.

The module 426 can be a component of the MR imaging system 100 or the MRI scanner 102 configured to generate a T1MAP image, proton density map (PDMAP) image or enhanced T1 weighted (T1WE) image using the TE1 k-space dataset corresponding to the k-space portion 406 and the TE1 k-space dataset corresponding to the k-space portion 414. Specifically, the module 426 can generate the T1MAP image, the PDMAP image or the T1WE image as described in U.S. patent Ser. No. 15/659,353 entitled "SYSTEMS AND METHODS FOR STRATEGICALLY ACQUIRED GRADIENT ECHO IMAGING." The T1WE, T1Map or PDMAP images generated by module 426 have higher signal-to-noise ratio (SNR) compared to corresponding images generated using TE1 k-space data associated with a single flip angle. The module 426 can be a software component executable by the processor 104, a hardware component or circuit, or a combination of software and hardware components. The module 426 can be a component of the MRI system 100 or the MR scanner 102.

In some implementations, the MRI scanner 102 or the imaging system 100 may acquire only TE2 k-space datasets (e.g., datasets corresponding to k-spaces portions 410, 418 and 420) at STEPs 302 and 304, and generate the k-space $S_{\theta 1, \theta 2, TE2}$. For instance, in applications where the goal is to generate SWI, tSWI or QSM images, the imaging system 100 may omit acquiring TE1 k-space datasets at STEPs 302 and 304.

The method 300 can include the MRI scanner 102 or the processor 102 reconstructing an MR image of the anatomical region of interest using the fifth MR k-space dataset generated at STEP 306 (STEP 308). The processor 104 can apply an inverse Fourier transform to the generated k-space $S_{\theta 1, \theta 2, TE2}$ (or the k-space dataset $S_{\theta 1, \theta 2, TE2}(k)$) to generate the MR image $Y_{\theta 1, \theta 2, TE2}$. As discussed above, the generated MR image has a higher resolution than an MR image constructed using only the TE2 k-space dataset acquired at STEP 302 or an MR image constructed using only the TE2 k-space dataset acquired at STEP 304. The constructed MR image can be processed or used to generate an SWI image, tSWI image, or a QSM image, among others.

Figure 4B:
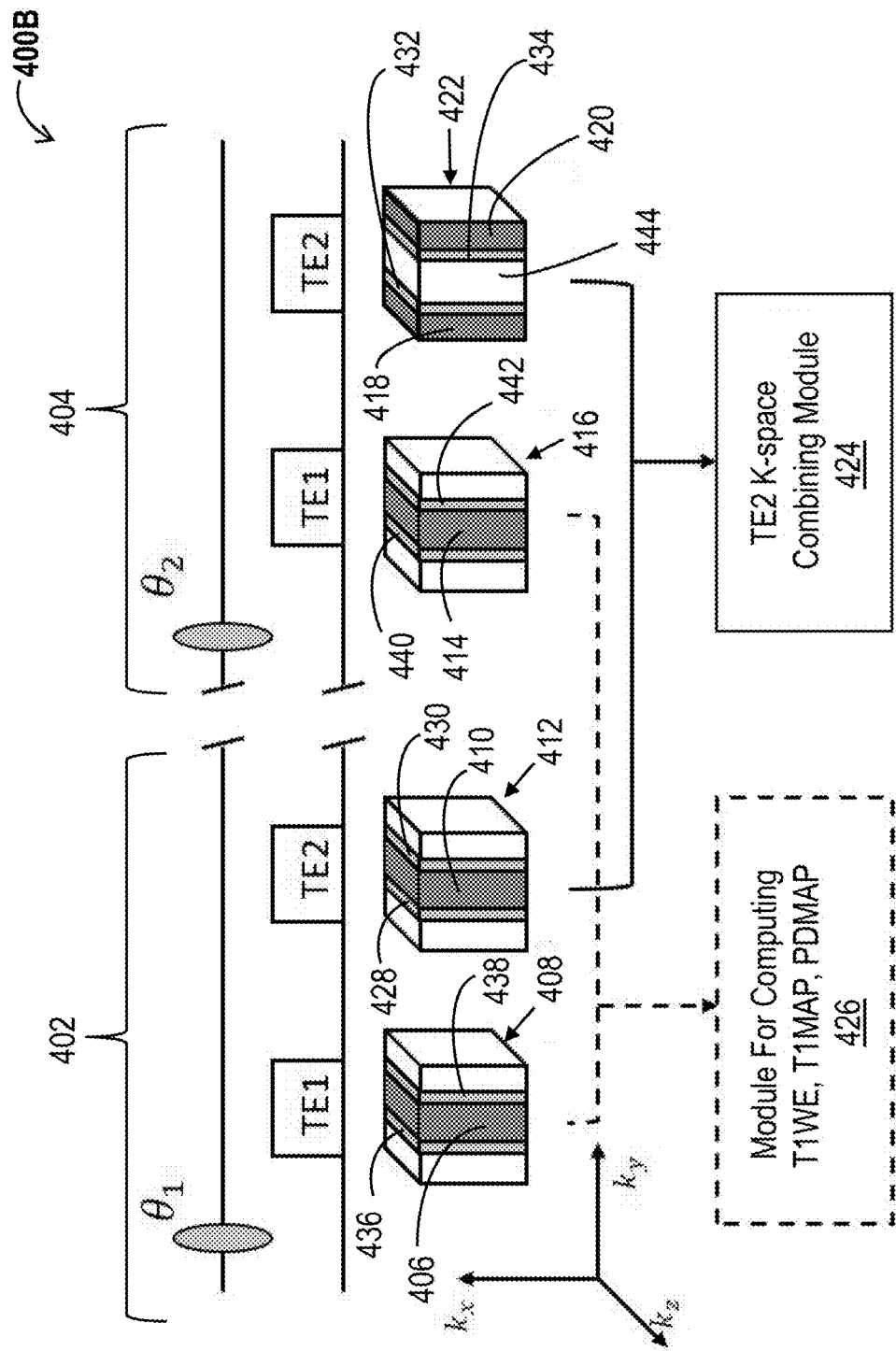

Referring now to FIG. 4B, a block diagram 400B depicting another example embodiment for acquiring and combining MR data corresponding to multiple flip angles is shown, according to inventive concepts of this disclosure. The diagram 400B is similar to the block diagram 400A except that in the block diagram 400B the TE2 k-space portion 410 of the TE2 k-space 412 (corresponding to the second flip angle $\theta_1$) partially overlaps with the TE2 k-space portions 418 and 420 of the TE2 k-space 422 (corresponding to the second flip angle $\theta_2$). Specifically, the TE2 k-space portion 410 can include the boundary regions or segments 428 and 430 (shown in light gray). The TE2 k-space portion 418 of the TE2 k-space 422 can include the boundary region or segment 432, which overlaps with the boundary region or segment 428 of the TE2 k-space 412. The TE2 k-space portion 420 of the TE2 k-space 422 can include the boundary region or segment 434, which overlaps with the boundary region or segment 430 of the TE2 k-space 412. The boundary regions or segments 428 and 432 (shown in light gray) can be represented by voxels having indices k between $-n\Delta k_y$ and $(-n+p-1)\Delta k_y$ along the $k_y$ axis. Also, the boundary regions or segments 430 and 434 (shown in light gray) can be represented by voxels having indices k between $(n-p)\Delta k_y$ and $(n-1)\Delta k_y$ along the $k_y$ axis. The boundary segments 428, 430, 432 and 434 can be viewed as having a width equal to $p\Delta k_y$, where p is an integer of choice.

In terms of the MR data acquisition, the MRI scanner 102 can acquire TE2 k-space data $S_{\theta1,TE2}(k)$ for $-n\Delta k_y \leq k \leq (n-1)\Delta k_y$ along the $k_y$ axis during the first block 402 of the dual-echo GRE sequence. During the second block 404 of the dual-echo GRE sequence, the MRI scanner 102 can acquire TE2 k-space data $S_{\theta2,TE2}(k)$ for $-L\Delta k_y \leq k \leq (-n+p-1)\Delta k_y$ and $(n-p)\Delta k_y \leq k \leq (L-1)\Delta k_y$ along the $k_y$ axis. As such, the k-space coverage of the TE2 k-space data $Y_{\theta1,TE2}(k)$ and the k-space coverage of the TE2 k-space data $S_{\theta2,TE2}(k)$ have overlapping data corresponding to the pair of boundary segments 428 and 432 and the pair of boundary segments 430 and 434. The data overlap can help smooth the transition from TE2 k-space data $S_{\theta1,TE2}(k)$ to TE2 k-space data $S_{\theta2,TE2}(k)$ when combined and used to generate an MR image.

The MRI scanner 102 or the processor 104 can combine the datasets $S_{\theta1,TE2}(k)$ and $S_{\theta2,TE2}(k)$ acquired at STEPs 302 and 304 as:

$$S_{\theta_1,\theta_2,TE2}(k) = \begin{cases} S_{\theta_2,TE2}(k); & \text{for } -L\Delta k_y \leq k \leq -(n+1)\Delta k_y \\ a_1 S_{\theta_1,TE2}(k) + a_2 S_{\theta_2,TE2}(k); & \text{for } -n\Delta k_y \leq k \leq (-n+p-1)\Delta k_y \\ S_{\theta_1,TE2}(k); & \text{for } (-n+p)\Delta k_y \leq k \leq (n-p)\Delta k_y \\ b_1 S_{\theta_1,TE2}(k) + b_2 S_{\theta_2,TE2}(k); & \text{for } (n-p+1)\Delta k_y \leq k \leq (n-1)\Delta k_y \\ S_{\theta_2,TE2}(k); & \text{for } n\Delta k_y \leq k \leq (L-1)\Delta k_y \end{cases} \quad (2)$$

As depicted in equation (2), the MRI scanner 102 or the processor 104 can use weighted sums of $S_{\theta1,TE2}(k)$ and $S_{\theta2,TE2}(k)$ to determine $S_{\theta1,\theta2,TE2}(k)$ within each voxel of the overlap regions or segments. In equation (2), the coefficients $a_1$ and $a_2$ can be defined as $$a_1 = \frac{k + n\Delta k_y}{p\Delta k_y}$$

and $a_2 = 1 - a_1$. Also, the coefficients $b_1$ and $b_2$ can be defined as $b_1 = 1 - b_2$, and $$b_2 = \frac{(n-1)\Delta k_y - k}{p\Delta k_y}.$$

The weighted sum approach used to combine $S_{\theta1,TE2}(k)$ and $S_{\theta2,TE2}(k)$ within the overlap regions or segments allows for a smooth transition between $S_{\theta1,TE2}(k)$ data and $S_{\theta2,TE2}(k)$ data. In some implementations, other mathematical weightings for the coefficients could be used.

In some implementations, the MRI scanner 102 or the processor 104 can use phase difference between the acquired dataset (e.g., corresponding to region 406 of FIG. 4A or regions 406, 436 and 438 of FIG. 4B) for the first TE1 k-space $S_{\theta1,TE2}$ 408 and the acquired dataset (e.g., corresponding to region 410 of FIG. 4A or regions 410, 428 and 430 of FIG. 4B) for the first TE2 k-space $S_{\theta1,TE2}$ 412 as well as the acquired dataset (e.g., corresponding to region 414 of FIG. 4A or regions 414, 440 and 442 of 4B) for the second TE1 k-space $S_{\theta2,TE1}$ 416 to determine the central portion 444 of the second TE2 k-space $S_{\theta2,TE2}$ 422. Note that the phase difference between the TE1 k-space and the TE2 k-space is the same for both flip angles $\theta_1$ and $\theta2$. That is the phase difference between the first TE1 k-space $S_{\theta1,TE1}$ 408 and the first TE2 k-space $S_{\theta1,TE2}$ 412 is the same as the phase difference between the second TE1 k-space $S_{\theta2,TE1}$ 416 and the second TE2 k-space $S_{\theta2,TE2}$ 422.

The MRI scanner 102 or the processor 104 can apply the inverse Fourier transform to the acquired dataset for the first TE1 k-space $S_{\theta1,TE1}$ 408 to generate a corresponding MR image. The MRI scanner 102 or the processor 104 can apply the inverse Fourier transform to the acquired dataset for the first TE2 k-space $S_{\theta1,TE2}$ 412 to generate a corresponding MR image. The MRI scanner 102 or the processor 104 can complex divide the MR image corresponding to the acquired dataset for the first TE1 k-space $S_{\theta1,TE2}$ 408 by the MR image corresponding to the acquired dataset for the first TE2 k-space $S_{\theta1,TE2}$ 412 to determine a phase difference and a T2* weighting factor. The MRI scanner 102 or the processor 104 can apply inverse Fourier transform to the acquired dataset (e.g., region 414 in FIG. 4A or regions 414, 440 and 442 of FIG. 4B) for the second TE1 k-space $S_{\theta2,TE1}$ 416 to generate a corresponding MR image, and then adjust the MR image corresponding to the acquired dataset for the second TE1 k-space $S_{\theta2,TE1}$ 416 using the phase difference and the T2* weighting factor. Specifically, the MRI scanner 102 or the processor 104 can multiply the MR image corresponding to the acquired dataset for the second TE1 k-space $S_{\theta2,TE1}$ 416 by the T2* weighting factor and the phase term $e^{-i\phi(y)}$, where $\phi(y)$ represents the phase difference between the MR image corresponding to the acquired dataset for the first TE1 k-space $S_{\theta1,TE1}$ 408 and the MR image corresponding to the acquired dataset for the first TE2 k-space $S_{\theta1,TE2}$ 412.

The MRI scanner 102 or the processor 104 can apply the Fourier transform to the adjusted MR image to generate corresponding k-space data. The k-space data corresponding to the adjusted MR image, which can be viewed as a central extrapolation of the acquired MR k-space dataset for the second TE1 k-space $S_{\theta2,TE1}$ 416, represents an estimate of the central region 428 or 444 of the second TE2 k-space $S_{\theta2,TE2}$ 422. The MRI scanner 102 or the processor 104 can combine the k-space data corresponding to the adjusted MR image and the acquired k-space dataset (e.g., regions 418 and 420 of FIG. 4A or regions 418, 420, 432 and 434 of FIG.

4B) for the second TE2 k-space $S_{\theta2,TE2}$ 422. The combining of these k-space datasets results in full data for the second TE2 k-space $S_{\theta2,TE2}$ 422.

The k-space dataset corresponding to the adjusted MR image and the acquired k-space dataset (e.g., regions 418 and 420 of FIG. 4A or regions 418, 420, 432 and 434 of FIG. 4B) for the second TE2 k-space $S_{\theta2,TE2}$ 422 may be disjoint (e.g., no overlap). In such cases, the MRI scanner 102 or the processor 104 can combine the two k-space datasets as described in relation to equation (1), except that the k-space dataset corresponding to the adjusted MR image is used instead of $S_{\theta_1,TE2}(k)$. However, if the k-space dataset corresponding to the adjusted MR image and the acquired k-space dataset (e.g., regions 418 and 420 of FIG. 4A or regions 418, 420, 432 and 434 of FIG. 4B) for the second TE2 k-space $S_{\theta2,TE2}$ 422 overlap, the MRI scanner 102 or the processor 104 can combine the two k-space datasets as described in relation to equation (2), except that the k-space dataset corresponding to the adjusted MR image is used instead of $S_{\theta_1,TE2}(k)$.

Approach II

Figure 5:
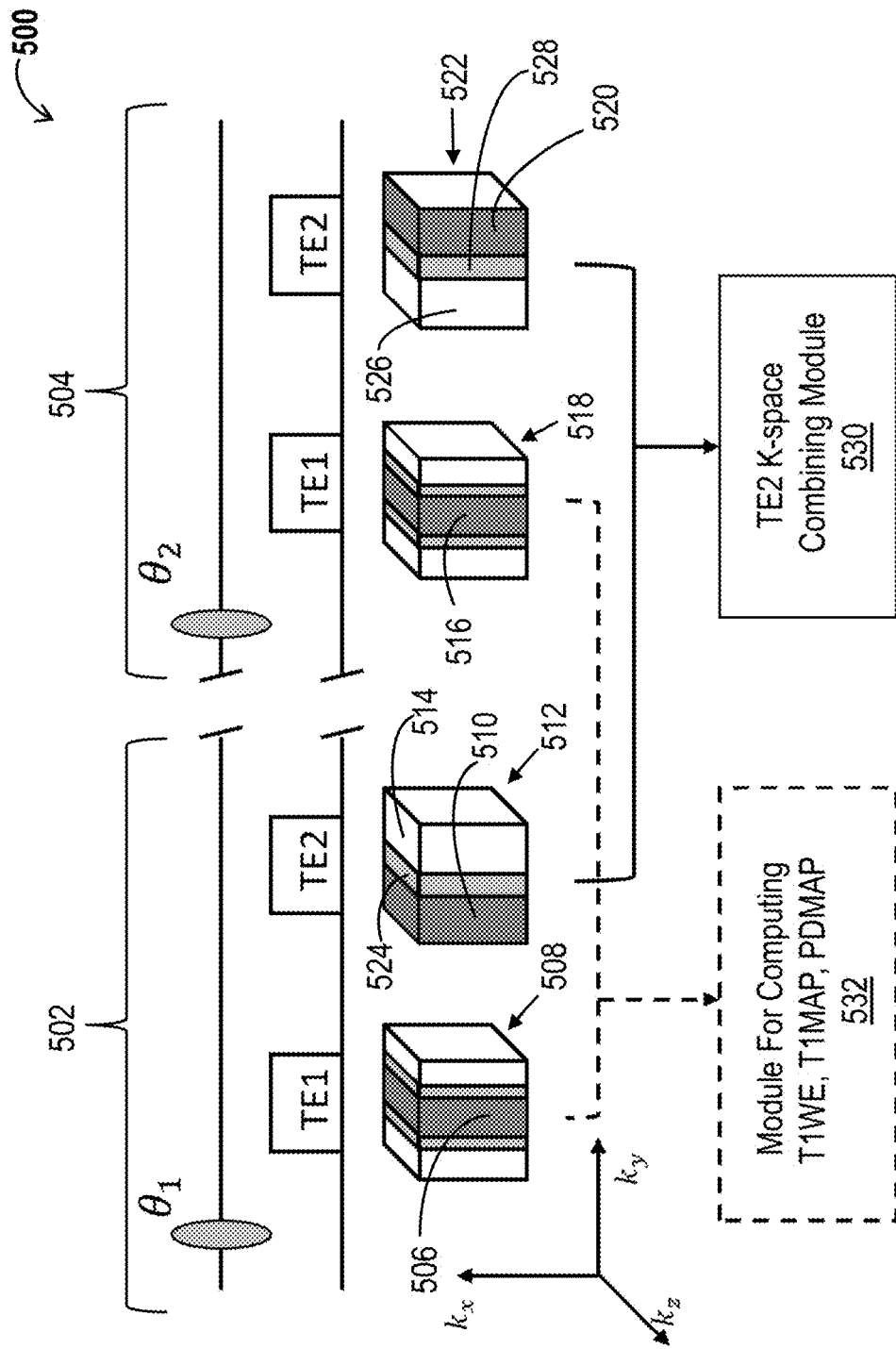
FIG. 5 shows a block diagram depicting another example approach for acquiring and combining MR data corresponding to multiple flip angles, according to inventive concepts of this disclosure.

Referring now to FIG. 5, a block diagram 500 depicting another example embodiment for acquiring and combining MR data corresponding to multiple flip angles is shown, according to inventive concepts of this disclosure. The diagram 500 illustrates two blocks 502 and 504 of a dual-echo GRE sequence. The first block 502 corresponds to the first flip angle $\theta_1$, while the second block 504 corresponds to the second flip angle $\theta_2$. During the first block 504 of the dual-echo GRE sequence, the MRI scanner 102 can acquire a first TE1 k-space dataset representing a central portion 506 of the corresponding TE1 k-space 508, and acquire a first TE2 k-space dataset representing a first side portion 510 of the corresponding TE2 k-space 512. The MRI scanner 102 can omit (or skip) acquiring TE2 k-space data corresponding to the k-space region 514 (shown in white). During the second block 504, the MRI scanner 102 can acquire a second TE1 k-space dataset representing a central portion 516 of the corresponding TE1 k-space 518, and acquire a second TE2 k-space dataset representing a second side portion 520 of the corresponding TE2 k-space 522. The MRI scanner 102 can omit (or skip) acquiring TE2 k-space data corresponding to the k-space region 526 (shown in white). The first and second side portions 510 and 520 can be opposite to one another.

In some implementations, the first and second side portions 510 and 520 can partially overlap. For instance, the first side portion 510 can include a first boundary or overlap region 524 (shown in light gray), and the second side portion 520 can include a second boundary or overlap region 528 (shown in light gray). The first and second boundary or overlap regions 524 and 528 can fully overlap with one another. The first side portion 510 can be defined as the set of points (k) where $-L\Delta k_y \leq k < q\Delta k_y$, and the first boundary or overlap region 524 can be defined as the set of points (k) where $-q\Delta k_y \leq k < q\Delta k_y$. Here q is an integer and the width of the first boundary or overlap region 524 is equal to $2q\Delta k_y$. The second side portion 520 can be defined as the set of points (k) where $-q\Delta k_y \leq k \leq (L-1)\Delta k_y$, and the second boundary or overlap region 528 can be defined as (similar to the first overlap region 524) the set of points (k) where $-q\Delta k_y \leq k < q\Delta k_y$.

The TE2 k-space combining module 530 can be a component of the imaging system 100 or the MRI scanner 102. The TE2 k-space combining module 530 can be a software component (e.g., executable by the processor 104), a hardware component or circuit, or a combination of both. The module 532 can be similar to the module 426 of FIGS. 4A and 4B. Similar to FIGS. 4A and 4B, let $S_{\theta_1,TE2}$ be the TE2 k-space 512 corresponding to the first flip angle $\theta_1$, and let $S_{\theta2,TE2}$ represent the TE2 k-space 522 corresponding to the second flip angle $\theta_2$. The TE2 k-space dataset corresponding to the k-space portion 510 can be defined as the $S_{\theta_1,TE2}(k)$ for $-L\Delta k_y \leq k < q\Delta k_y$. The TE2 k-space dataset corresponding to the k-space portion 520 can be defined as the $S_{\theta2,TE2}(k)$ for $-q\Delta k_y \leq k < (L-1)\Delta k_y$. The TE2 k-space combining module 530 (or the processor 104) can combine these k-space datasets (STEP 306 of method 300) to generate the fifth k-space dataset $S_{\theta2,\theta2,TE2}(k)$ as:

$$S_{\theta_1,\theta_2,TE2}(k) = \begin{cases} S_{\theta_1,TE2}(k); & \text{for } -L\Delta k_y \leq k < -q\Delta k_y \\ c_1 S_{\theta_1,TE2}(k) + c_2 S_{\theta_2,TE2}(k); & \text{for } -q\Delta k_y \leq k < q\Delta k_y \\ S_{\theta_2,TE2}(k); & \text{for } q\Delta k_y \leq k < (L-1)\Delta k_y \end{cases} \quad (3)$$

In equation (3), the coefficients $c_1$ and $c_2$ can be set equal to 0.5.

The data overlap along the pair of boundary segments 524 and 528 can result in phase discrepancy within the boundary segments when combining the TE2 k-space data $S_{\theta_1,TE2}(k)$ and the TE2 k-space data $S_{\theta2,TE2}(k)$ and using $S_{\theta_1,\theta_2,TE2}(k)$ to generate an MR image. To address this issue, the MRI scanner 102 or the processor 104 can adjust the phase data for any of the MR images corresponding to $S_{\theta_1,TE2}(k)$ and $S_{\theta2,TE2}(k)$ prior to combining the k-space datasets $S_{\theta_1,TE2}(k)$ and $S_{\theta2,TE2}(k)$ within the overlap regions or segments. Specifically, prior to combining the datasets $S_{\theta_1,TE2}(k)$ and $S_{\theta2,TE2}(k)$ within the overlap regions or segments, the MRI scanner 102 or the processor 104 can compare the phase of the images that result from each of these k-space datasets. The MRI scanner 102 or the processor 104 can fill the regions outside the collected data for each k-space with zeroes until the k-space is full and then take the inverse Fourier transform of $S_{\theta_1,TE2}(k)$ and $S_{\theta2,TE2}(k)$ to generate two images $U_{\theta_1,TE2}(y)$ and $U_{\theta2,TE2}(y)$. The MRI scanner 102 or the processor 104 can compare the phase information of the images $U_{\theta_1,TE2}(y)$ and $U_{\theta2,TE2}(y)$, for example, by complex dividing $U_{\theta2,TE2}(y)$ by $U_{\theta_1,TE2}(y)$ to determine $e^{i\varphi(y)}$ where $\varphi(y)$ represents the phase difference. The MRI scanner 102 or the processor 104 can adjust the phase information of $U_{\theta2,TE2}(y)$ by computing $V_{\theta2,TE2}(y) = e^{-i\varphi(y)} U_{\theta2,TE2}(y)$ so that both images $U_{\theta_1,TE2}(y)$ and $V_{\theta2,TE2}(y)$ have the same phase information. The MRI scanner 102 or the processor 104 can apply the Fourier transform to $V_{\theta2,TE2}(y)$ to compute the corresponding k-space $T_{\theta2,TE2}(k)$. The k-space $T_{\theta2,TE2}(k)$ can be viewed as a modified (or processed) version of $S_{\theta2,TE2}(k)$.

Now, the MRI scanner 102 or the processor 104 can generate the k-space $S_{\theta_1,\theta_2,TE2}(k)$ by combining the k-space datasets $S_{\theta_1,TE2}(k)$, $S_{\theta2,TE2}(k)$ and $T_{\theta2,TE2}(k)$ as:

$$S_{\theta_1,\theta_2,TE2}(k) = \begin{cases} S_{\theta_1,TE2}(k); & \text{for } -L\Delta k_y \leq k < -q\Delta k_y \\ d_1 S_{\theta_1,TE2}(k) + d_2 T_{\theta_2,TE2}(k); & \text{for } -q\Delta k_y \leq k < q\Delta k_y \\ T_{\theta_2,TE2}(k); & \text{for } q\Delta k_y \leq k < (L-1)\Delta k_y \end{cases} \quad (4)$$

Equation (4) is similar to equation (3), except for the use of $T_{\theta2,TE2}(k)$ instead of $S_{\theta2,TE2}(k)$ within the overlap boundary region where $-q\Delta k_y \leq k < q\Delta k_y$. Specifically, in equation (4), the coefficients $d_1$ and $d_2$ can be set equal to 0.5 similar to the coefficients $c_1$ and $c_2$ of equation (3). Correcting for any phase difference eliminates or mitigates undesired image artifacts due to such phase difference. In some implementations, the MRI scanner 102 or the processor 104 can adjust the phase information of $U_{\theta1,TE2}(y)$ (instead of $U_{\theta1,TE2}(y)$) and use the corresponding k-space $T_{\theta1,TE2}(k)$ instead of $T_{\theta2,TE2}(k)$ in equation (4). The processor 104 can apply an inverse Fourier transform to the generated k-space data $S_{\theta1,\theta2,TE2}(k)$ to generate the MR image $Y_{\theta1,\theta2,TE2}$.

Approach III

Figure 6:
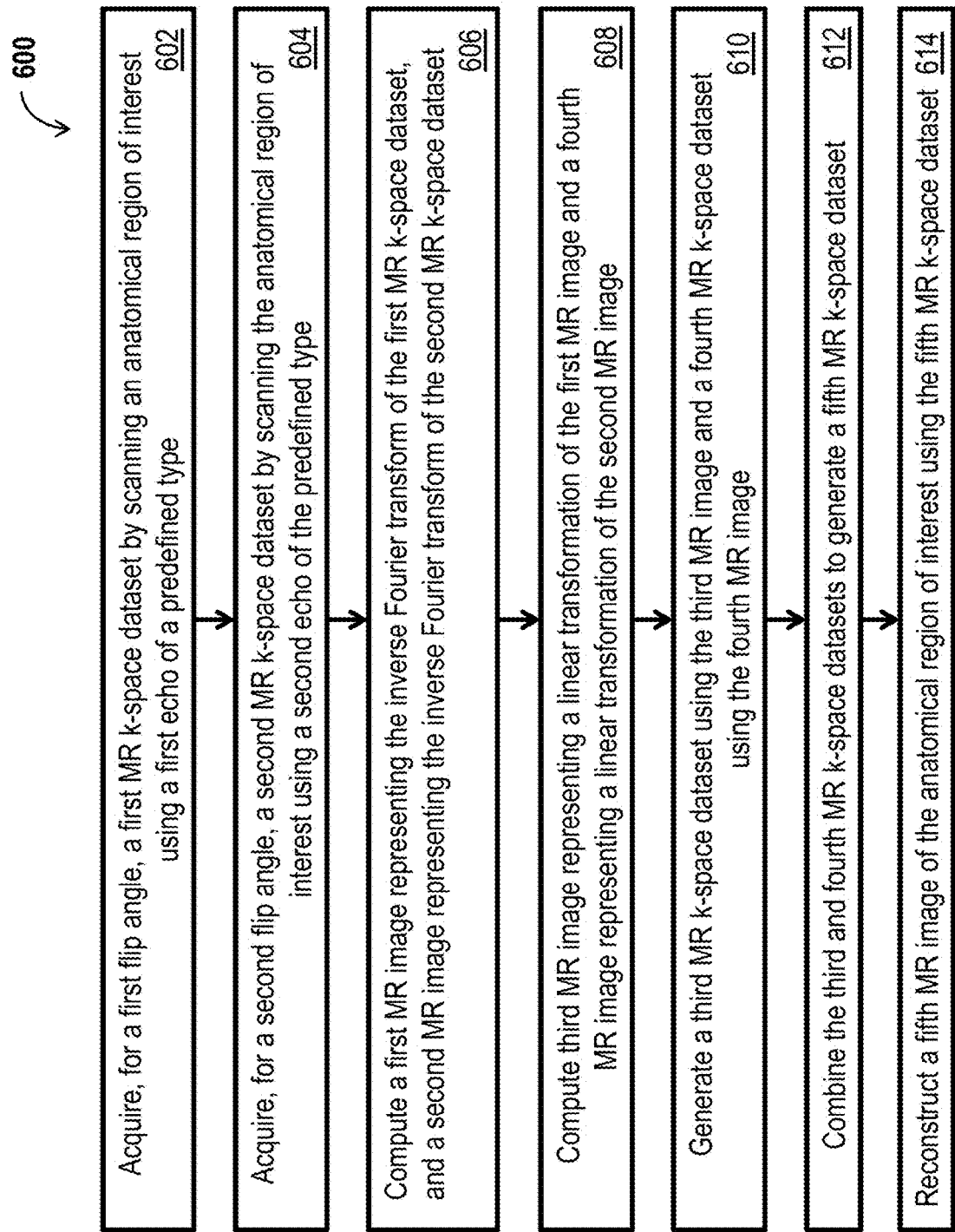
FIG. 6 is a flowchart illustrating yet another example approach of strategically acquired gradient echo (STAGE) imaging, according to inventive concepts of this disclosure.

Referring to FIG. 6, a flowchart illustrating another method 600 of STAGE imaging using MR data corresponding to multiple flip angles is shown, according to inventive concepts of this disclosure. The method 600 can include acquiring, for a first flip angle, a first MR k-space dataset of an anatomical region of interest using a first echo of a predefined type (STEP 602), and acquiring, for a second flip angle, a second MR k-space dataset of the anatomical region of interest using a second echo of a predefined type (STEP 604). The method 600 can include computing a first MR image representing an inverse Fourier transform of the first MR k-space dataset and a second MR image representing an inverse Fourier transform of the second MR k-space dataset (STEP 606). The method 600 can include computing a third MR image representing a linear transformation of the first MR image and a fourth MR image representing a linear transformation of the second MR image (STEP 608). The method 600 can include generating a third MR k-space dataset using the third MR image and a fourth MR k-space dataset using the fourth MR image (STEP 610). The method 600 can include combining the third and fourth MR k-space datasets to generate a fifth MR k-space dataset (STEP 612), and reconstructing a fifth MR image of the anatomical region of interest using the fifth k-space dataset (STEP 614).

The method 600 can include the MRI scanner acquiring, for a first flip angle, a first MR k-space dataset $S_{\theta1,TEn}(k)$ of an anatomical region of interest using a first echo of a predefined type such as TEn (STEP 602), and acquiring, for a second flip angle, a second MR k-space dataset $S_{\theta2,TEn}(k)$ of the anatomical region of interest using a second echo of the predefined type (STEP 604). As discussed above with regard to FIGS. 3-5, the MRI scanner 102 can trigger a first dual-echo (or multi-echo) GRE sequence having a first block (e.g., block 402 or 502) associated with the first flip angle $\theta_1$ and a second block (e.g., block 404 or 504) associated with the second flip angle $\theta_2$. The MRI scanner 102 can acquire the first MR k-space dataset $S_{\theta1,TEn}(k)$ during the first block of the dual echo (or multi-echo) GRE sequence, and acquire the second MR k-space dataset $S_{\theta2,TEn}(k)$ during the second block of the dual echo (or multi-echo) GRE sequence. Each of the first and second MR k-space datasets $S_{\theta1,TEn}(k)$ and $S_{\theta2,TEn}(k)$ can represent a portion of the corresponding k-space (e.g., does not fully cover the corresponding k-space but only a portion thereof) as discussed with regard to FIGS. 3-5.

Unlike method 300 where the first and second MR k-space datasets are TE2 k-space datasets, here the first and second MR k-space datasets can be both TE1 k-space datasets, both TE2 k-space datasets, both TE3 k-space datasets, both TE4 k-space datasets, or a combination of k-space datasets associated with different types of echo times, among others. MR images corresponding to k-space datasets associated with different flip angles can have distinct visual characteristics. Specifically, the intensities (or average intensities) associated with different tissue types and/or the contrast between the different tissue types may vary in MR images corresponding to distinct flip angles.

Figure 7:
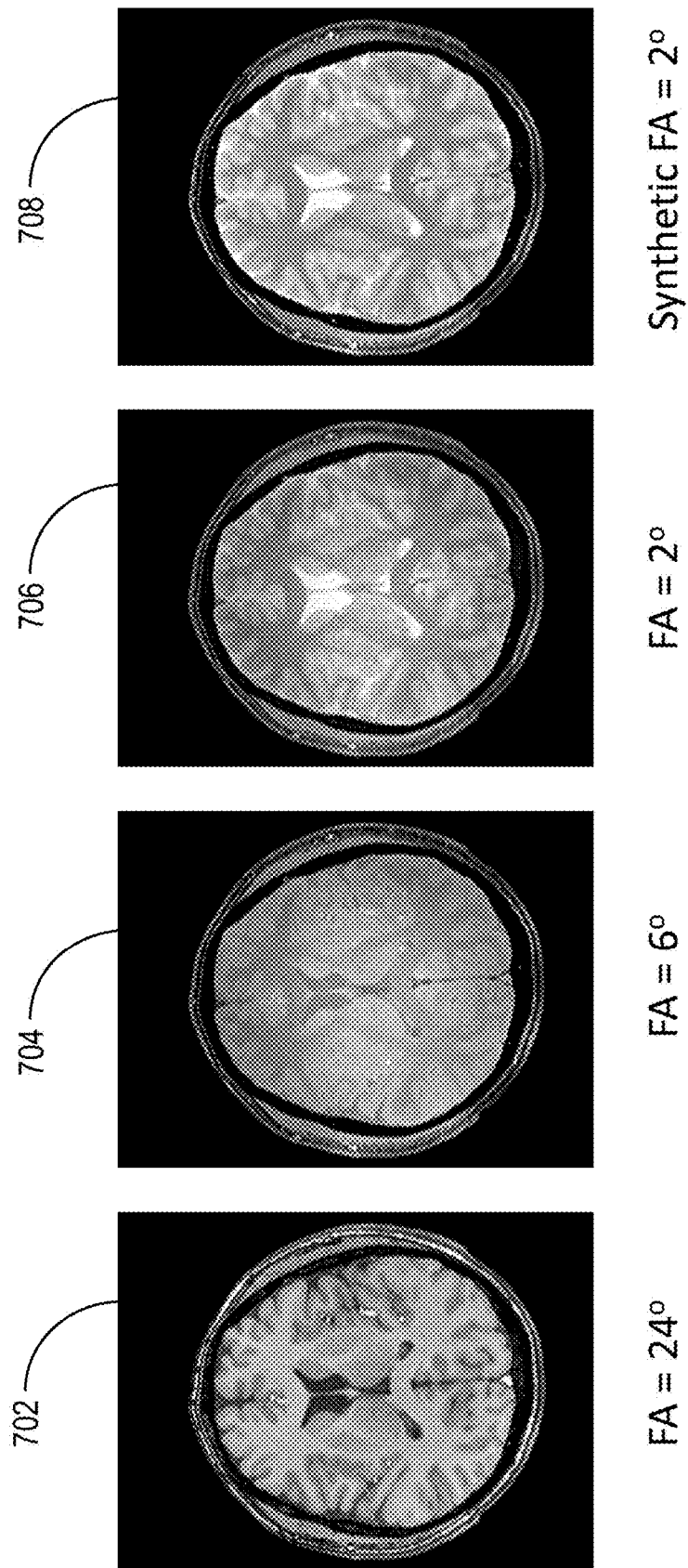
FIG. 7 shows various MR brain images corresponding to distinct flip angles for TE1 data are shown.

Referring to FIG. 7, various MR brain images corresponding to distinct flip angles for the TE1 data are shown. The brain image 702 is generated using TE1 data corresponding to a flip angle equal to 24 degrees, the brain image 704 is generated using TE1 data corresponding to a flip angle equal to 6 degrees, and the brain image 706 is generated using TE1 data corresponding to a flip angle equal to 2 degrees. In the brain image 702 corresponding to the high flip angle 24 degrees, the white matter has the highest intensity, the gray matter has the next highest intensity, and the cerebral spinal fluid (CSF) has the lowest intensity. When considering the brain image 706 or 708 corresponding to the 2° flip angle, the CSF has the highest intensity, the gray matter has the next highest intensity, and the white matter has the lowest intensity. This is not true, however, for the brain image 704 corresponding to the 6° flip angle. The difference in signal intensities between the MR image 702 and the MR image 706 or 708 is due to the fact that the water content dominates the low flip angle image 706 or 708 and the CSF is basically 100% water, the gray matter is about 84% water, and the white matter is about 68% water.

Unlike brain images 706 and 708, the brain image 704 corresponding to the 6° flip angle does not show contrast in intensities between the three brain regions opposite to corresponding contrast shown in brain image 702. However, the MRI scanner 102 or the processor 104 can use acquired datasets corresponding to flip angles 24° and 6° to generate T1maps and PDmaps as described in U.S. patent Ser. No. 15/659,353 entitled "SYSTEMS AND METHODS FOR STRATEGICALLY ACQUIRED GRADIENT ECHO IMAGING." Once the T1maps and PDmaps are generated, the MRI scanner 102 or the processor 104 can simulate or generate the synthetic image for any flip angle. Hence, the MRI scanner 102 or the processor 104 can generate the synthetic image for the 2° flip angle, such as image 708, using the T1maps and PDmaps. The MRI scanner 102 or the processor 104 can use the synthetic image for the 2° flip angle, instead of the image corresponding to the 6° flip angle, in the rest of the steps of the method 600. As illustrated in FIG. 7, the simulated or synthetic image 708 corresponding to a 2° flip angle looks identical to the image 706 actually acquired at a 2° flip angle except that it may have higher signal-to-noise ratio.

The variation, based on the flip angle, in contrast and signal intensities for the various brain regions calls for processing MR datasets corresponding to distinct flip angles before combining such datasets. For instance, by subtracting from each of the MR images 702 and 708 (or 706, e.g., if the small flip angle is equal to 2°) the corresponding baseline, the resulting images would have opposite contrasts. As such, scaling one of the images (with removed baseline) can cause the two images to look similar. Specifically, by applying proper negative scaling to one of the MR images (after baseline subtraction), the contrast between any two tissue types can be made similar (e.g., to some extent) across the two MR images. With respect to combining MR k-space datasets corresponding to distinct flip angles, the second echo MR k-space datasets can be modified, before combining them, such that the corresponding MR images have relatively similar contrasts between different tissue types. Such processing prior to combining the MR k-space datasets can lead to a reduction of artifacts in the MR image obtained from the combined k-space.

Referring back to FIG. 6, the method 600 can include the MRI scanner 102 or the processor 104 computing a first MR image representing the inverse Fourier transform of the first MR k-space dataset, and a second MR image representing the inverse Fourier transform of the second MR k-space dataset (STEP 606). Transforming the first and second MR k-space datasets to image data can allow for determining the processing to be performed on the MR images so that the processed images have similar visual characteristics for the different tissue types. For instance, the transformation from the k-space domain to the image domain (or the spatial domain) allows for determining the adjustment to be made to the intensities, the contrasts or other visual characteristics of the MR images so that the various tissue types look similar in the adjusted MR images.

The method 600 can include the MRI scanner 102 or the processor 104 computing a third image representing a linear transformation of the first MR image (or a linear transformation of another image associated with the first MR image), and fourth MR image representing a linear transformation of the second MR image (STEP 608). For example, let $X_{\theta1,TEn}(y)$ be the MR image representing the inverse Fourier Transform of $S_{\theta1,TEn}(k)$ and let $X_{\theta2,TEn}(y)$ be the MR image representing the inverse Fourier transform of $S_{\theta2,TEn}(k)$. As discussed above with regard to FIG. 7, if the first flip angle $\theta_1$ is not small enough (e.g., 6°), the MRI scanner 102 or the processor 104 can use a synthetic (or simulated) MR image $X_{\theta1',TEn}(y)$ for a smaller flip angle $\theta_1'$ (e.g., 2°) instead of the MR image $X_{\theta1,TEn}(y)$. In the following, the angle $\theta_s$ represents either the flip angle $\theta_1$ or the flip angle $\theta_1'$ and $X_{\theta s,TEn}(y)$ represents either the MR image $X_{\theta1,TEn}(y)$ or the MR image $X_{\theta1',TEn}(y)$ depending on, for example, how small is the flip angle $\theta_1$ and which MR image is used for further processing. The MRI scanner 102 or the processor 104 can determine for each of the MR images $X_{\theta s,TEn}(y)$ and $X_{\theta2,TEn}(y)$ a respective baseline value, such as a value for some particular tissue of interest. Let $\beta_1$ be the baseline value for $X_{\theta s,TEn}(y)$ and let (32 be the baseline value for $X_{\theta2,TEn}(y)$. The MRI scanner 102 or the processor 104 can compute $\beta_1$ as the CSF value in $X_{\theta s,TEn}(y)$, and can compute (32 as the CSF value in $X_{\theta2,TEn}(y)$. The MRI scanner 102 or the processor 104 can subtract, from each of the MR images $X_{\theta s,TEn}(y)$ and $X_{\theta2,TEn}(y)$ the respective baseline value to compute $Z_{\theta s,TEn}(y)=|X_{\theta s,TEn}(y)-\beta_1|$ and $Z_{\theta2,TEn}(y)=X_{\theta2,TEn}(y)-\beta_2$.

The MRI scanner 102 or the processor 104 can determine for at least one of the MR images (e.g., after baseline subtraction) a respective scaling factor $\alpha$. The scaling factor $\alpha$ can be viewed as a proportionality value between the peak intensity of one MR image and the peak intensity in the other MR image. In some implementations, the MRI scanner 102 or the processor 104 can determine the scaling factor as $$\alpha = \frac{\max(z_{\theta s,TEn})}{\max(z_{\theta2,TEn})}.$$

The MRI scanner 102 or the processor 104 can transform the MR image $X_{\theta s,TEn}(y)$ to $Z_{\theta s,TEn}(y)=X_{\theta s,TEn}(y)-\beta_1$ and transform the MR image $X_{\theta2,TEn}(y)$ to $Z'_{\theta2,TEn}(y)=\alpha Z_{\theta2,TEn}(y)=a(X_{\theta2,TEn}(y)-\beta_2)$.

In general the MRI scanner 102 or the processor 104 can transform the MR image $X_{\theta s,TEn}$ to $Z_{\theta s,TEn}=\alpha_1 (X_{\theta s,TEn}-\beta_1)$ and transform the MR image $X_{\theta2,TEn}$ to $Z'_{\theta2,TEn}=\alpha_2 (X_{\theta2,TEn}-\beta_2)$, where $\alpha_1$ and $\alpha_2$ represent two scaling factors. The MRI scanner 102 or the processor 104 can determine the parameters $\alpha_1$, $\alpha_2$, $\beta_1$ and $\beta_2$ such that the adjusted (or processed) MR images $Z_{\theta s,TEn}$ and $Z'_{\theta2,TEn}$ have similar visual characteristics (e.g., similar intensities for each type of tissue). For example, the MRI scanner 102 or the processor 104 can determine the parameters $\alpha_1$, $\alpha_2$, $\beta_1$ and $\beta_2$ such that the MR images $Z_{\theta s,TEn}$ and $Z'_{\theta s,TEn}$ have equal maximum intensities, equal minimum intensity, equal maximum contrast, or equal maximum contrast between a given pair of tissue types, among others.

The method 600 can include the MRI scanner 102 or the processor 104 generating a third k-space dataset corresponding to the third MR image representing the linear transformation of the first MR image (or the linear transformation of another MR image associated with the first MR image), and a fourth k-space dataset corresponding to the fourth MR image representing the linear transformation of the second MR image (STEP 610). For instance, the MRI scanner 102 or the processor 104 can generate the third MR k-space dataset $W_{\theta s,TEn}(k)$ as the Fourier transform of the MR image $Z_{\theta s,TEn}(y)$, and can generate the fourth MR k-space dataset $W_{\theta2,TEn}(k)$ as the Fourier transform of the MR image $Z'_{\theta2,TEn}(y)$. In general, the MRI scanner 102 or the processor 104 can transform the third and fourth MR images back to the k-space domain.

The method 600 can include the MRI scanner 102 or the processor 104 combining the third and fourth MR k-space datasets to generate a fifth MR k-space dataset (STEP 612). The MRI scanner 102 or the processor 104 can combine the third and fourth MR k-space datasets in a similar way as discussed above with regard to FIGS. 2-5. For example, the third and fourth MR k-space datasets can correspond to distinct k-space portions as those described in, or discussed with regard to FIGS. 4A, 4B and 5. Also, as discussed above with regard to FIGS. 2-5, the k-space portions corresponding to the third and fourth MR k-space datasets can partially overlap (e.g., similar to partial overlap described in, and discussed with regard to, FIGS. 4B and 5). The combining of the third and fourth MR k-space datasets $W_{\theta s,TEn}(k)$ and $W_{\theta2,TEn}(k)$ can be performed according to any of the techniques described above in equations (1)-(4) except for the fact that the third, fourth and fifth k-space datasets can be associated with any echo time and are not restricted to TE2. For instance, where $W_{\theta s,TEn}(k)$ and $W_{\theta2,TEn}(k)$ are combined similarly to equation (3) above, the MRI scanner 102 or the processor 104 can generate a new fully covered k-space $W_{\theta s, \theta2,TEn}(k)$ as:

$$W_{\theta_s,\theta_2,TEn}(k) = \begin{cases} W_{\theta_s,TEn}(k); & \text{for } -L\Delta k_y \le k < -q\Delta k_y \\ e_1 W_{\theta_{s_1},TEn}(k) + e_2 W_{\theta_2,TEn}(k); & \text{for } -q\Delta k_y \le k < q\Delta k_y \\ W_{\theta_2,TEn}(k); & \text{for } q\Delta k_y \le k < (L-1)\Delta k_y \end{cases} \quad (5)$$

where the constants $e_1$ and $e_2$ are set to 0.5 similar to the constants $c_1$ and $c_2$ of equation (3). Equation (3) of Approach II can be viewed as a special case of equation (5) with n=2 and $\theta_s$ equal to $\theta_1$.

In some implementations, the MRI scanner 102 or the processor 104 can apply phase adjustment before combining $W_{\theta1,TE1}(k)$ and $W_{\theta2,TE1}(k)$ within the overlap region as discussed above with regard to equation (4). For instance, the MRI scanner 102 or the processor 104 can complex divide $Z_{\theta s,TEn}(y)$ by $Z'_{\theta2,TEn}(y)$ to determine $e^{i\phi(y)}$ where $\phi(y)$ represents the phase difference. The MRI scanner 102 or the processor 104 can adjust the phase information of $Z'_{\theta2,TEn}(y)$ by computing $V_{\theta2,TEn}(y)=e^{-\phi(y)}Z'_{\theta2,TEn}(y)$ so that both images $Z_{\theta s,TEn}(y)$ and $V_{\theta2,TEn}(y)$ have the same phase information. The MRI scanner 102 or the processor 104 can apply the Fourier transform to $V_{\theta2,TEn}(y)$ to compute the corresponding k-space $T_{\theta2,TEn}(k)$. The MRI scanner 102 or the processor 104 can generate the k-space $W_{\theta s,\theta 2,TEs}(k)$ by combining the k-space datasets $W_{\theta s,TEn}(k)$, $W_{\theta 2,TEn}(k)$ and $Z'_{\theta 2,TEn}(k)$ as:

$$W_{\theta_s,\theta_2,TEn}(k) = \begin{cases} W_{\theta_s,TEn}(k); & \text{for } -L\Delta k_y \leq k < -q\Delta k_y \\ f_1 W_{\theta_s,TEn}(k) + f_2 T_{\theta_2,TEn}(k); & \text{for } -q\Delta k_y \leq k < q\Delta k_y \\ W_{\theta_2,TEn}(k); & \text{for } q\Delta k_y \leq k < (L-1)\Delta k_y \end{cases} \quad (6)$$

where the constants $f_1$ and $f_2$ are set to 0.5 similar to the constants $e_1$ and $e_2$ of equation (5). Equation (4) of Approach II can be viewed as a special case of equation (6) with n=2 and $\theta_s$ equal to $\theta_1$.

The method 600 can include the MRI scanner 102 or the processor 104 reconstructing an MR image of the anatomical region of interest using the fifth MR k-space dataset (STEP 614). The MRI scanner 102 or the processor 104 can apply the inverse Fourier transform to the $W_{\theta s,\theta 2,TEn}(k)$ dataset to reconstruct the now high resolution complex MR image $Y_{\theta s,\theta 2,TEn}(y)$ of the anatomical region of interest. One can then add back a final constant to the image $Y_{\theta s,\theta 2,TEn}(y)$ equal to the baseline value $\beta_1$ that was originally subtracted from $X_{\theta s,TEn}(y)$. Using the phase information from this image, the MRI scanner 102 or the processor 104 can create a new HR SWI STAGE image.

In general, the MRI scanner 102 or the processor 104 can employ APPROACH III to generate a spin density weighted image or a T1 weighted image, when the first and second echo times associated with the first and second k-space datasets are TE1 echo times, or to generate a susceptibility weighted image or a quantitative susceptibility mapping (QSM) image when the first and second echo times associated with the first and second k-space datasets are TE2 echo times. In the case that there are multiple echoes, this process of merging k-space data sets can be done for any or all desired echoes. The exact implementation will depend on how k-space is collected at each echo. An example implementation can include breaking up each echo into an equal number of k-space lines chosen to fill in the missing k-space lines desired for the final high resolution image.

Figure 8:
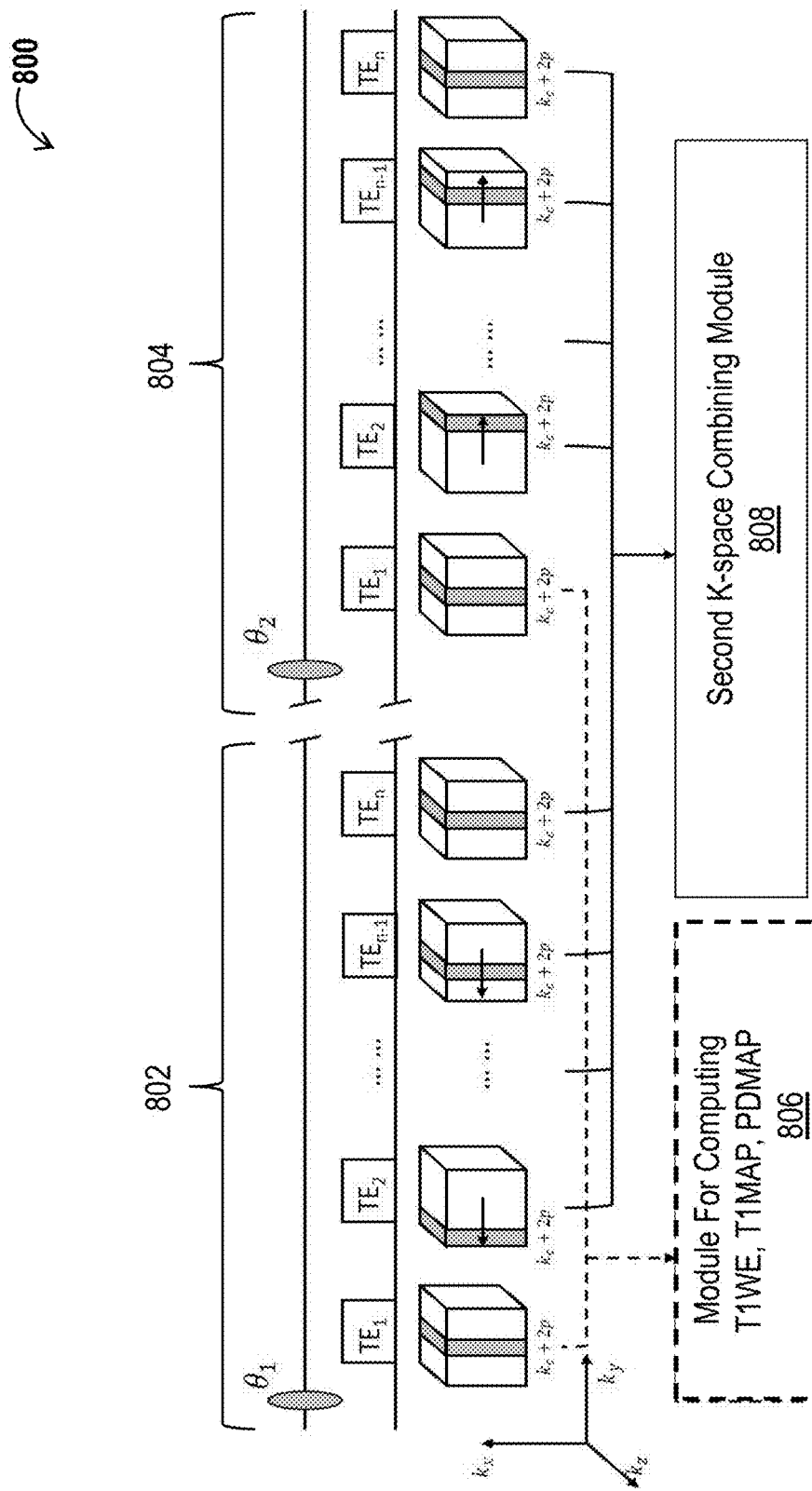
FIG. 8 shows a block diagram depicting yet another example approach for acquiring and combining MR data corresponding to multiple flip angles, according to inventive concepts of this disclosure.

Referring to FIG. 8, a block diagram 800 depicting another example approach for acquiring and combining multi-echo MR data corresponding to multiple flip angles is shown, according to inventive concepts of this disclosure. The block diagram 800 illustrates an example multi-echo implementation of STAGE imaging. The MRI scanner 102 can trigger a multi-echo GRE sequence having two blocks 802 and 804. The first multi-echo GRE sequence block 802 corresponds to a first flip angle $\theta_1$, while the second multi-echo GRE sequence block 804 corresponds to a second flip angle $\theta_2$. The second flip angle $\theta_2$ can be greater than the first flip angle $\theta_1$. For example, the first flip angle $\theta_1$ can be equal to 6 degrees, while the second flip angle $\theta_2$ can be equal to 24 degrees. For each of the multi-echo GRE sequence blocks 802 and 804, the MRI scanner 102 can acquire partial MR k-space datasets (shown in gray strips) at each echo time of a plurality of echo times TE1, TE2, . . . , TEn, where n is an integer.

The implementation described in FIG. 8 can be viewed as extending the idea of STAGE imaging to a multi-echo mode. The MRI scanner 102 or the processor 104 can use the TE1 k-space datasets across the multi-echo GRE sequence blocks 802 and 804 to form T1 weighted enhanced (T1WE), T1, proton spin density (PD), $B_1^+$ and/or $B_1^-$ mapping images of relatively high signal to noise ratio (SNR). On the other hand, the MRI scanner 102 or the processor 104 can combine the k-space datasets associated with higher echo times (e.g., TE2, TE3, TE4, TEn), that are acquired across the multi-echo GRE sequence blocks 802 and 804, to form higher resolution phase images for use in creating SWI, tSWI and/or QSM images.

The second k-space combining module 808 can combine the k-space datasets acquired at the echo times TE2, TE3, TE4, . . . , TEn in the multi-echo GRE sequence blocks 802 and 804 to form a higher resolution final k-space dataset for use to generate an MR image. For instance, the MRI scanner 102 or the processor 104 can setup the k-space center at a certain echo (e.g., TEn in FIG. 8) other than the first echo to dominate the susceptibility contrast. The second k-space combining module 808 can use, for example, all echoes other than the first echo for filling a high-resolution k-space by a center-out phase encoding design to get an effective phase encoding equal to $nk_c$. The first echo and the echo for the SWI k-space center can be encoded for the strip consisting of the central $k_c+2p$ lines of the k-space, where p represents the number of overlapping lines in k-space for each of the remaining n−2 echoes. The remaining n−2 echoes of each flip angle can each be encoded for a respective strip having $k_c/2+p$ lines of k-space. As depicted in FIG. 8, in the first multi-echo GRE sequence block 802 corresponding to the first flip angle, the strips corresponding to the n−2 echoes TE2 . . . TE(n−1) echoes can be arranged on one side (e.g., to the left) of the strip corresponding to the TEn echo. In the second multi-echo GRE sequence block 804 corresponding to the second flip angle, the strips corresponding to the n−2 echoes TE2 . . . TE(n−1) echoes can be arranged on the other side (e.g., to the right) of the strip corresponding to the TEn echo. The second k-space combining module 808 can combine k-space datasets acquired across the multi-echo GRE sequence blocks 802 and 804 according to any of the methods described above with regard to FIGS. 2-7.

While in FIG. 8, the second k-space combining module 808 is designed or configured to combine the k-space datasets acquired at the echo times TE2, TE3, TE4, . . . , TEn in the multi-echo GRE sequence blocks 802 and 804, according to a more general implementation, the second k-space combining module 808 can use any combination of the k-space datasets acquired at all the echo times (including TE1) across the multi-echo GRE sequence blocks 802 and 804. The second k-space combining module 808 or the processor 104 can apply some processing (e.g., as discussed with regard to FIG. 6) to the k-space datasets or the corresponding MR images before combining them. The MRI scanner 102 or the processor 104 can use any of the methods or techniques discussed above with regard to FIGS. 2-7 to generate the high resolution k-space dataset. The MRI scanner 102 or the processor can apply inverse Fourier transform to the high resolution k-space dataset to construct a higher resolution (or higher SNR) MR image of the anatomical region of interest.

In some implementations, the MRI scanner 102 or the processor 104 can execute a combination of the STAGE imaging methods or approaches described above with regard to FIGS. 2-8. For example, the MRI scanner 102 or the processor 104 can employ the STAGE imaging approach described with regard to FIGS. 3-5 to enhance or increase the resolution of echo data associated with echo times other than TE1, and use the STAGE imaging approach to enhance or increase the resolution of TE1 echo (or any other echo) data. The imaging system 100 or the MRI scanner 102 can execute any of these STAGE imaging approaches with either no or minimal increase in execution time. However, by combining these methods using a conventional segmented k-space acquisition as shown in FIG. 8, the data can either be acquired in half the time, or the resolution can be doubled (or increased) yet again, or the slice thickness cut in half (while doubling the number of slices) at no further expense in time. In some implementations, the imaging system 100 or the MRI scanner 102 can implement these STAGE imaging concepts by using short echo time separations with more echoes. In some implementations, the imaging system 100 or the MRI scanner 102 can apply these STAGE imaging concepts with other fast MR imaging methods, such as parallel imaging and compressed sensing.

To validate the STAGE imaging approaches described above, one can compare MR images constructed using these imaging approaches to images constructed using acquired high resolution k-space data. The comparison can allow for visualization and quantification of the reproducibility of high resolution data by merging or combining relatively low resolution k-space datasets corresponding to different flip angles (see FIGS. 9 and 10).

Figure 9:
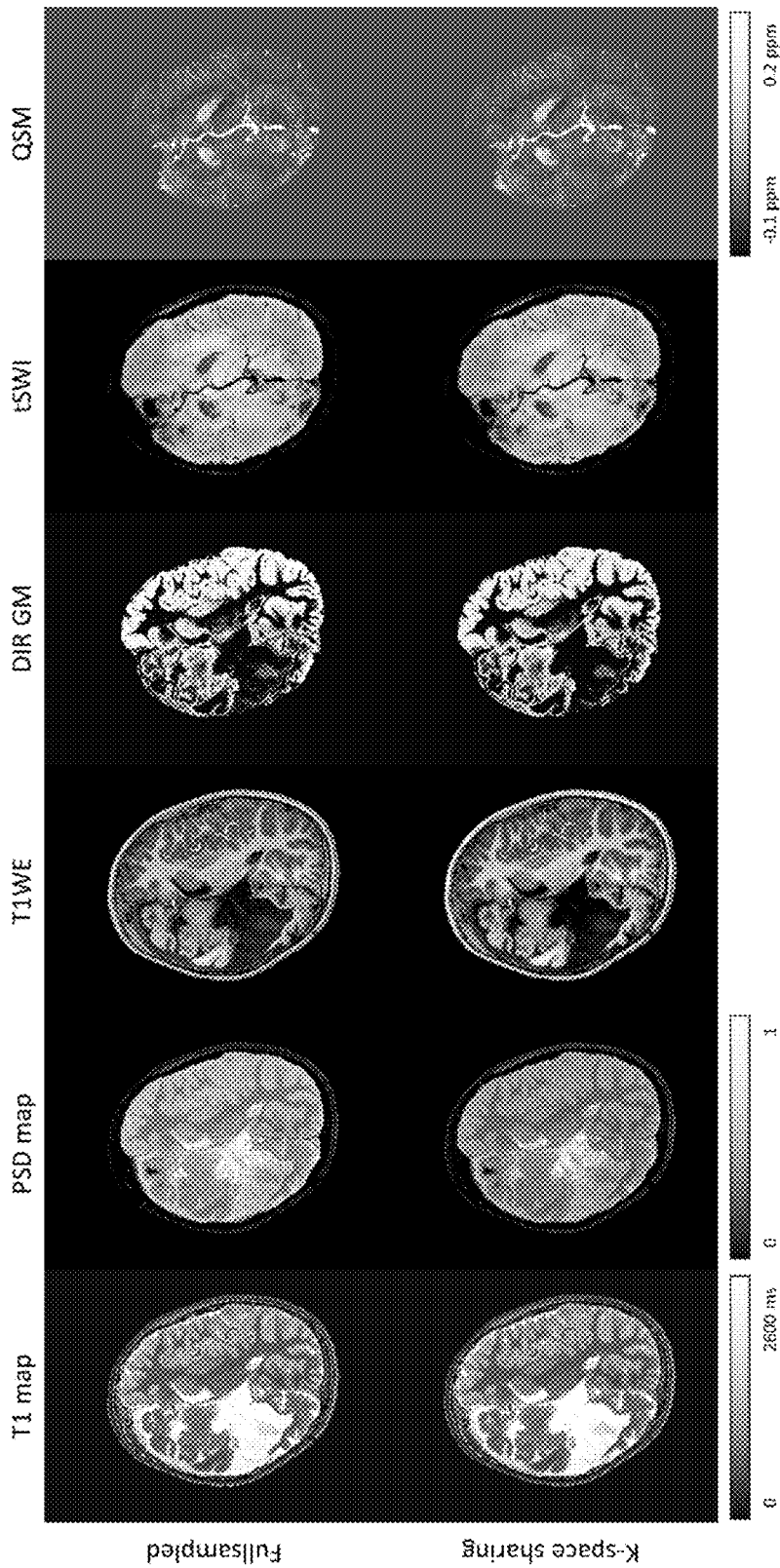
FIG. 9 shows STAGE imaging simulation results for various types of MR images.

Referring to FIG. 9, STAGE imaging simulation results for various types of MR images are shown. The first row of images corresponds to fully sampled original data. Specifically, the first row shows T1 map, PD map, T1WE, simulated double inversion recovery (DIR) GM, tSWI, and QSM images, where each of which is constructed using a respective fully acquired k-space. The second row shows corresponding MR images reconstructed using k-space datasets acquired at two flip angles (6 and 24 degrees). The MR data is acquired by scanning the brain of a patient with Sturge-Weber syndrome (SWS) (10y1m, male). T1 map, PD map and T1WE images of the second row have an overall SNR increase of 62.9% than the corresponding MR images in the first row. The SNR is computed by manually drawn multiple regions on WM region. The tSWI and QSM images in the second row are visually very close to the corresponding images in the first row but were acquired in an equivalent of half the original time. The tSWI and QSM images show minimum intensity projection (mIP) for tSWI and a maximum intensity projection (MIP) for QSM both over 8 slices.

Figure 10:
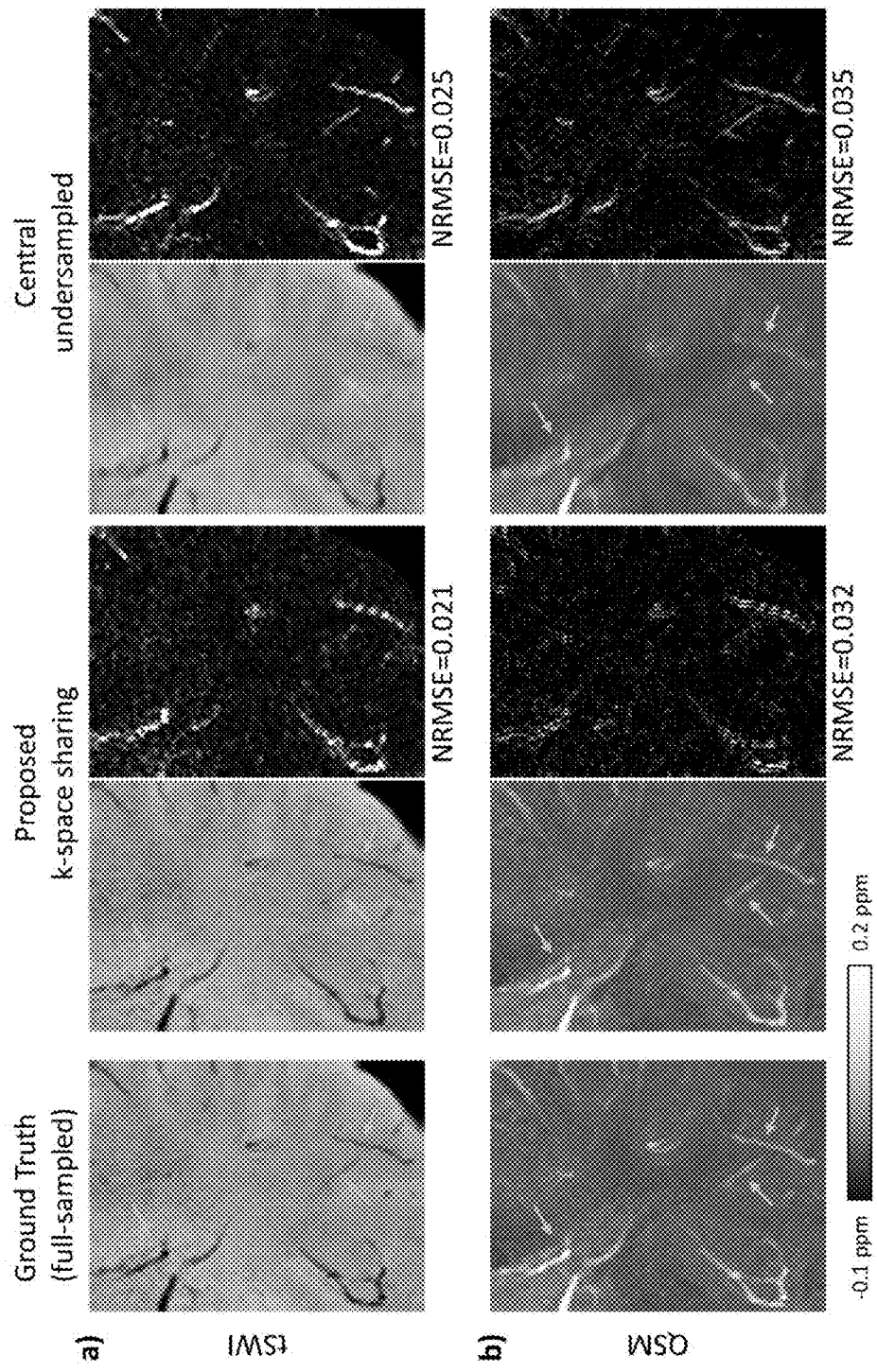
FIG. 10 shows STAGE imaging simulation results illustrating the advantages of k-space merging of the two second echoes from each of the different flip angles.

FIG. 10 shows STAGE imaging simulation results for tSWI images and QSM images. FIG. 10 shows three sets of SWI and QSM data consisting of fully-sampled MR data acting as ground truth (GT), k-space sharing ($Y_{\theta 1,\theta 2,TE2}(y)$) data referring to MR images constructed by combining various k-space datasets, and central undersampled ($U_{\theta 1,\theta 2,TE2}(y)$) data. In comparing these MR data sets, one can use a voxel based normalized root mean square error (NRMSE), $NRMSE_{U,Y}=\sqrt{((GT-U,Y_{\theta 1,\theta 2,TE2}(y))^2/(GT^2))}$. A brain mask generated from the QSM reconstruction can be used for the NRMSE calculation. The NRMSE number for each image represents the average of those from all voxels in the entire volume such as the brain, for example.

The central undersampled data in FIG. 10 represent MR data acquired with 50% central undersampling. The MR images are mIP/MIP over 8 slices. At the visual level, the $Y_{\theta 1,\theta 2,TE2}(y)$ images show better quality compared to the $U_{\theta 1,\theta 2,TE2}(y)$ images. Specifically, the veins pointed to by the arrows are more visible in the $Y_{\theta 1,\theta 2,TE2}(y)$ images than in the $U_{\theta 1,\theta 2,TE2}(y)$ images. In fact, the visibility of the veins in the $Y_{\theta 1,\theta 2,TE2}(y)$ images is similar to that in the GT images. Also, at the quantitative level, the NRMSE values are smaller for the $Y_{\theta 1,\theta 2,TE2}(y)$ images than for the $U_{\theta 1,\theta 2,TE2}(y)$ images, which indicates that the $Y_{\theta 1,\theta 2,TE2}(y)$ images are closer to the GT images than the $U_{\theta 1,\theta 2,TE2}(y)$ images.

The methods and system described herein provide various techniques for generating improved images of anatomical regions scanned using two or more flip angles and two or more echo times. These methods and systems should not be interpreted as limited to human brain and can be used for other anatomical regions or organs. Also, while the figures depict three-dimensional (3D) k-spaces, the imaging approaches and techniques described herein also apply to two-dimensional (2D) MR data. Furthermore, the methods and system described herein may be used to construct other types of MR images than those disclosed herein. In addition, the imaging system 100 or the MRI scanner 102 can implement any combination of the methods or processes described herein.

A person skilled in the art should appreciate that processes described in this disclosure can be implemented using computer code instructions executable by a processor, such as processor 104. The computer code instructions can be stored on a non-transitory or tangible computer-readable medium such as the memory 106. The memory 106 can be a random access memory (RAM), a read only memory (ROM), a cache memory, a disc memory, any other memory, or any other computer readable medium. Processes described in this disclosure can be implemented by an apparatus including at least one processor and/or memory storing executable code instructions. The code instructions when executed by the at least one processor can cause performing any of the processes or operations described in this disclosure. The apparatus can be, for example, the MRI scanner 102, a computer device or other electronic device associated with the MRI scanner 102.

What is claimed is:

1. A magnetic resonance imaging (MRI) system comprising:
    an MRI scanner configured to:
    acquire, for a first flip angle, a first magnetic resonance (MR) k-space dataset and a second MR k-space dataset by scanning an anatomical region of interest with at least two echo times, the first MR k-space dataset acquired at a first TE1 echo time and the second MR k-space dataset acquired at a first TE2 echo time;
    acquire, for a second flip angle different from the first flip angle, a third MR k-space dataset and a fourth MR k-space dataset by scanning the anatomical region of interest with the at least two echo times, the third MR k-space dataset acquired at a second TE1 echo time different from the first TE1 echo time and the fourth MR k-space dataset acquired at a second TE2 echo time different from the first TE2 echo time;
    at least one processor; and
    a memory, with computer code instructions stored thereon, the computer code instructions, when executed by the at least one processor, cause the at least one processor to:
        generate a fifth MR k-space dataset by combining the fourth MR k-space dataset with either (i) the second MR k-space dataset or (ii) a central extrapolation of the third MR k-space dataset; and
        reconstruct an MR image of the anatomical region of interest using the fifth MR k-space dataset.

2. The MRI system of claim 1, wherein the at least one processor is further configured to reconstruct a susceptibility-weighted image using the MR image of the anatomical region of interest.

3. The MRI system of claim 1, wherein the at least one processor is further configured to reconstruct a quantitative susceptibility mapping (QSM) image using the MR image of the anatomical region of interest.

4. The MRI system of claim 1, wherein combining the second MR k-space dataset and the fourth MR k-space dataset includes:
  using the second MR k-space dataset to generate a central portion of the fifth MR k-space dataset; and
  using the fourth MR k-space dataset to generate two opposite outer portions of the fifth MR k-space dataset.

5. The MRI system of claim 4, wherein the central portion of the modified third echo MR k-space dataset (i) partially overlaps with a first outer portion of the two opposite outer portions of the fifth MR k-space dataset along a first overlap region, and (ii) partially overlaps with a second outer portion of the two opposite outer portions of the fifth MR k-space dataset along a second overlap region.

6. The MRI system of claim 1, wherein the computer code instructions, when executed by the at least one processor, cause the at least one processor to:
  generate a second MR image by using an inverse Fourier transform of the first MR k-space dataset;
  generate a third MR image by using an inverse Fourier transform of the second MR k-space data set;
  complex divide the third MR image by the second MR image to obtain a phase difference image and a T2* weighting factor;
  generate a fourth MR image by using an inverse Fourier transform of the third MR k-space data set;
  adjust, using the phase difference image and the T2* weighting factor, the fourth MR image to generate a fifth MR image;
  Fourier transform the fifth MR image to obtain the central k-space extrapolation of the third MR k-space dataset;
  generate the fifth MR k-space dataset by combining the central extrapolation of the third MR k-space dataset and the fourth MR data k-space dataset, the central extrapolation of the third MR k-space dataset to generate a central portion of the fifth MR k-space dataset and the fourth MR k-space dataset used to generate two opposite outer portions of the fifth MR k-space dataset; and
  apply inverse Fourier transform to the fifth MR k-space dataset to reconstruct the MR image of the anatomical region of interest.

7. The MRI system of claim 6, wherein the central extrapolation of the third MR k-space dataset (i) partially overlaps with a first outer portion of the two opposite outer portions of the fifth MR k-space dataset along a first overlap region, and (ii) partially overlaps with a second outer portion of the two opposite outer portions of the fifth MR k-space dataset along a second overlap region.

8. The MRI system of claim 1, wherein combining the second MR k-space dataset and the fourth MR k-space dataset includes:
  using the second MR k-space dataset to generate a first side portion of the fifth MR k-space dataset; and
  using the fourth MR k-space dataset to generate a second side portion of the fifth MR k-space dataset, the first side portion opposite to the second side portion.

9. The MRI system of claim 6, wherein the first side portion of the fifth MR k-space dataset partially overlaps with the second side portion of the fifth MR k-space dataset along an overlap region.

10. The MRI system of claim 9, wherein in generating the fifth MR k-space dataset, the at least one processor is configured to:
  generate a second MR image by using an inverse Fourier transform of the second MR k-space data set;
  generate a third MR image by using an inverse Fourier transform of the fourth MR k-space data set;
  compare phase information of the second MR image to phase information of the third MR image;
  adjust, based on the comparison, the phase information of the third MR image so that the adjusted phase information of the third MR image is equal to the phase information of the second MR image;
  generate a sixth MR k-space dataset by applying a Fourier transform to the third MR image with the adjusted phase information; and
  generate the fifth MR k-space dataset by combining the second MR k-space dataset and the sixth MR k-space dataset within the overlap region.

11. The MRI system of claim 1, wherein the first flip angle is 6 degrees and the second flip angle is 24 degrees.

12. A method for magnetic resonance imaging (MRI), comprising:
  acquiring, by an MRI scanner, for a first flip angle, a first magnetic resonance (MR) k-space dataset and a second MR k-space dataset by scanning an anatomical region of interest with at least two echo times, the first MR k-space dataset acquired at a first TE1 echo time and the second MR k-space dataset acquired at a first TE2 echo time;
  acquiring, by the MRI scanner, for a second flip angle different from the first flip angle, a third MR k-space dataset and a fourth MR k-space dataset by scanning the anatomical region of interest with the at least two echo times, the third MR k-space dataset acquired at a second TE1 echo time different from the first TE1 echo time and the fourth MR k-space dataset acquired at a second TE2 echo time different from the first TE2 echo time;
  generating, by the MRI scanner, a fifth MR k-space dataset by combining the fourth MR k-space dataset and either (i) the second MR k-space dataset or (ii) a central extrapolation of the third MR k-space dataset; and
  reconstructing, by the MRI scanner, an MR image of the anatomical region of interest using the fifth MR k-space dataset.

13. The method of claim 12, further comprising reconstructing a susceptibility-weighted image or a quantitative susceptibility mapping (QSM) image using the MR image of the anatomical region of interest.

14. The method of claim 12, comprising:
  generating a second MR image by using an inverse Fourier transform of the first MR k-space dataset;
  generating a third MR image by using an inverse Fourier transform of the second MR k-space data set;
  complex dividing the third MR image by the second MR image to obtain a phase difference image and a T2* weighting factor;
  generating a fourth MR image by using an inverse Fourier transform of the third MR k-space data set;
  adjusting, using the phase difference image and the T2* weighting factor, the fourth MR image to generate a fifth MR image;
  Fourier transforming the fifth MR image to obtain the central extrapolation of the third MR k-space dataset;

generate the fifth MR k-space dataset by combining the central extrapolation of the third MR k-space dataset and the fourth MR data k-space dataset, the central extrapolation of the third MR k-space dataset to used generate a central portion of the fifth MR k-space dataset and the fourth MR k-space dataset used to generate two opposite outer portions of the fifth MR k-space dataset; and applying inverse Fourier transform to the fifth MR k-space dataset to reconstruct the MR image of the anatomical region of interest.

15. The method of claim 14, wherein the central extrapolation of the third MR k-space dataset (i) partially overlaps with a first outer portion of the two opposite outer portions of the fifth MR k-space dataset along a first overlap region, and (ii) partially overlaps with a second outer portion of the two opposite outer portions of the fifth MR k-space dataset along a second overlap region.

16. The method of claim 12, wherein combining the second MR k-space dataset and the fourth MR k-space dataset includes:

using the second MR k-space dataset to generate a central portion of the fifth MR k-space dataset; and using the fourth MR k-space dataset to generate two opposite outer portions of fifth MR k-space dataset.

17. The method of claim 16, wherein the central portion of the fifth MR k-space dataset (i) partially overlaps with a first outer portion of the two opposite outer portions of the fifth MR k-space dataset along a first overlap region, and (ii) partially overlaps with a second outer portion of the two opposite outer portions of the fifth MR k-space dataset along a second overlap region.

18. The method of claim 12, wherein combining the second MR k-space dataset and the fourth MR k-space dataset includes:

using the second MR k-space dataset to generate a first side portion of the fifth MR k-space dataset; and using the fourth MR k-space dataset to generate a second side portion of the fifth MR k-space dataset, the first side portion opposite to the second side portion.

19. The method of claim 17, wherein the first side portion of the fifth MR k-space dataset partially overlaps with the second side portion of the fifth MR k-space dataset along an overlap region.

20. The method of claim 18, wherein generating the fifth MR k-space dataset includes:

generating a second MR image by using a Fourier transform of the second MR k-space data set;

generating a third MR image by using a Fourier transform of the fourth MR k-space data set;

comparing phase information of the second MR image to phase information of the third MR image;

adjusting, based on the comparison, the phase information of the third MR image so that the adjusted phase information of the third MR image is equal to the phase information of the second MR image;

generating a sixth MR k-space dataset by applying an inverse Fourier transform to the third MR image with the adjusted phase information; and generating the fifth MR k-space dataset by combining the second MR k-space dataset and the sixth MR k-space dataset within the overlap region.

21. The method of claim 12, wherein the first flip angle is 6 degrees and the second flip angle is 24 degrees.

22. A non-transitory computer-readable medium comprising computer code instructions stored thereon, the computer code instructions when executed by at least one processor cause the at least one processor to:

cause a magnetic resonance imaging (MRI) scanner to acquire, for a first flip angle, a first magnetic resonance (MR) k-space dataset and a second 1\4R k-space dataset by scanning an anatomical region of interest with at least two echo times, the first MR k-space dataset acquired at a first TE1 echo time and the second MR k-space dataset acquired at a first TE2 echo time;

cause the MRI scanner to acquire, for a second flip angle different from the first flip angle, a third MR k-space dataset and a fourth MR k-space dataset by scanning the anatomical region of interest with the at least two echoes times, the third MR k-space dataset acquired at a second TE1 echo time different from the first TE1 echo time and the fourth MR k-space dataset acquired at a second TE2 echo time different from the first TE2 echo time;

generate a fifth MR k-space dataset by combining the fourth MR k-space dataset and either (i) the second MR k-space dataset or (ii) a central extrapolation of the third MR k-space dataset; and reconstruct an MR image of the anatomical region of interest using the fifth MR k-space dataset.

\* \* \* \* \*